(12) United States Patent
Schings

(10) Patent No.: US 12,702,417 B2
(45) Date of Patent: Aug. 11, 2026

(54) POWERED FIRING PLATFORM FOR LINEAR SURGICAL STAPLER

(71) Applicant: Cilag GmbH International, Zug (CH)

(72) Inventor: Brian D. Schings, Maineville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 90 days.

(21) Appl. No.: 18/500,711

(22) Filed: Nov. 2, 2023

(65) Prior Publication Data

US 2025/0143705 A1 May 8, 2025

(51) Int. Cl.

*A61B 17/068* (2006.01)
*A61B 17/072* (2006.01)
*A61B 17/11* (2006.01)
*A61B 17/115* (2006.01)
*A61B 17/00* (2006.01)

(52) U.S. Cl.

CPC .... *A61B 17/1114* (2013.01); *A61B 17/07207* (2013.01); *A61B 17/115* (2013.01); *A61B 2017/00017* (2013.01); *A61B 2017/00398* (2013.01)

(58) Field of Classification Search

CPC ............................ A61B 17/068; A61B 17/072
See application file for complete search history.

(56) References Cited

U.S. PATENT DOCUMENTS 2,892,457 A * 6/1959 Sturtz ............... A61M 5/31581 222/391
4,940,468 A * 7/1990 Petillo ................. A61F 9/00763 604/22
7,824,443 B2 * 11/2010 Salahieh ............... A61F 2/2439 623/2.11
7,922,064 B2 * 4/2011 Boyden ................ A61B 17/072 606/139
10,016,564 B2 * 7/2018 Piehl ....................... A61P 25/02
10,258,419 B2 * 4/2019 Auld ...................... A61B 34/30
10,631,866 B2 4/2020 Laurent et al.

(Continued)

FOREIGN PATENT DOCUMENTS

WO WO 2022/233036 A1 11/2022
WO WO 2023/010314 A1 2/2023

OTHER PUBLICATIONS

European extended Search Report and Written Opinion dated Nov. 28, 2024, for Application No. 24209394.6, 10 pages.

(Continued)

*Primary Examiner* — Gloria R Weeks
(74) *Attorney, Agent, or Firm* — FBT Gibbons LLP

(57) ABSTRACT

An apparatus that includes a body, an initiation device, an actuator, and a driver. The body has a cradle sized and configured to receive a linear surgical stapler operable to clamp and staple tissue with a plurality of staples. The actuator is in communication with the initiation device and the initiation device is coupled with the body. The driver is operatively coupled with the actuator and is configured to mechanically couple with a firing assembly of the linear surgical stapler. The initiation device is configured to be manipulated by a user to activate the actuator so that the actuator actuates the driver relative to the body, thereby driving the firing assembly distally to fire the linear surgical stapler.

20 Claims, 18 Drawing Sheets

(56) References Cited

U.S. PATENT DOCUMENTS

| | | | | |
|---|---|---|---|---|
| 10,639,111 | B2 * | 5/2020 | Kopp | A61B 34/25 |
| 10,667,818 | B2 | 6/2020 | McLain et al. | |
| 10,687,819 | B2 | 6/2020 | Stokes et al. | |
| 10,772,630 | B2 * | 9/2020 | Wixey | A61B 17/068 |
| 10,874,393 | B2 * | 12/2020 | Satti, III | A61B 17/1155 |
| 10,874,398 | B2 | 12/2020 | Baxter, III et al. | |
| 10,898,187 | B2 | 1/2021 | Deck et al. | |
| 10,905,419 | B2 | 2/2021 | Schings et al. | |
| 10,932,781 | B2 | 3/2021 | Jones et al. | |
| 11,033,266 | B2 | 6/2021 | Jones et al. | |
| 11,045,193 | B2 | 6/2021 | Schings et al. | |
| 11,219,454 | B2 | 1/2022 | Schings et al. | |
| 11,224,425 | B2 | 1/2022 | Schings et al. | |
| 11,229,433 | B2 | 1/2022 | Schings et al. | |
| 11,278,285 | B2 | 3/2022 | Deck et al. | |
| 11,660,089 | B2 * | 5/2023 | Shelton, IV | A61B 17/07207 227/180.1 |
| 11,937,812 | B2 | 3/2024 | Schings et al. | |
| 12,426,881 | B2 * | 9/2025 | Du | A61B 17/07207 |
| 12,449,224 | B2 * | 10/2025 | Yehle | F41B 5/10 |
| 2008/0296346 | A1 * | 12/2008 | Shelton, IV | A61B 34/71 227/180.1 |
| 2013/0289595 | A1 * | 10/2013 | Edwards | A61B 17/32002 606/170 |
| 2014/0005654 | A1 * | 1/2014 | Batross | A61B 17/320092 606/171 |
| 2015/0209821 | A1 * | 7/2015 | Pfahnl | A61M 5/31586 222/340 |
| 2019/0261991 | A1 * | 8/2019 | Beckman | A61B 17/1155 |
| 2020/0008798 | A1 * | 1/2020 | Evans | A61B 17/282 |
| 2020/0405408 | A1 * | 12/2020 | Shelton, IV | A61B 34/30 |
| 2021/0212684 | A1 * | 7/2021 | Satti, III | A61B 50/30 |
| 2021/0369272 | A1 | 12/2021 | Schings | |
| 2022/0142641 | A1 | 5/2022 | Wang | |
| 2023/0397911 | A1 | 12/2023 | Deck et al. | |
| 2025/0143705 | A1 * | 5/2025 | Schings | A61B 17/07207 |

OTHER PUBLICATIONS

Design U.S. Appl. No. 29/842,580, entitled "Staple Cartridge for a Linear Surgical Stapler," Filed Jun. 14, 2022.

Design U.S. Appl. No. 29/842,581, entitled "Linear Surgical Stapler," Filed Jun. 14, 2022.

* cited by examiner

POWERED FIRING PLATFORM FOR LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be manually actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
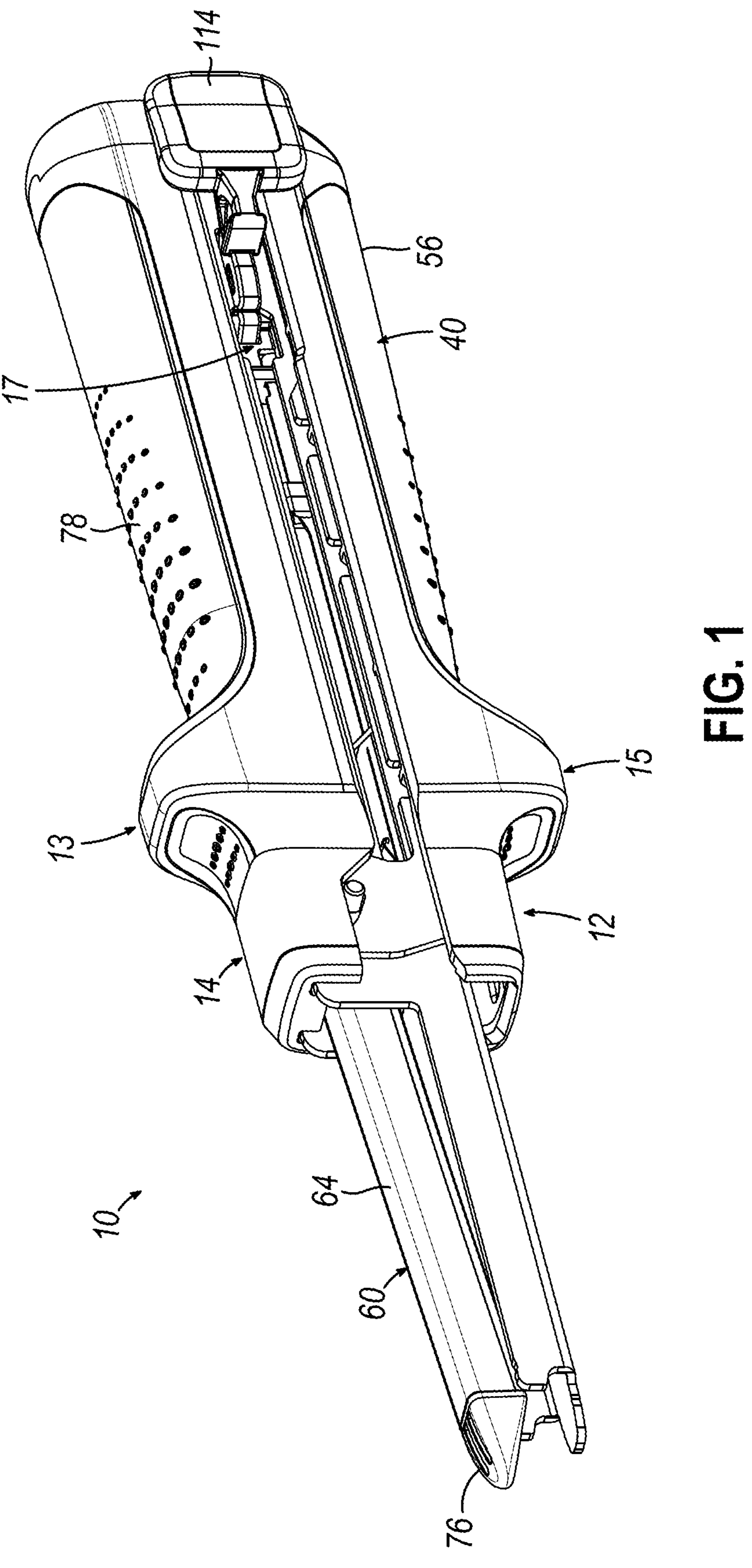
FIG. 1 depicts a perspective view of an illustrative linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms "about" and "approximately" as used herein in connection with any numerical values or ranges indicate a suitable dimensional tolerance that allows the referenced feature(s) to function for its intended purpose as described herein.

I. Illustrative Linear Surgical Stapler

A. Overview of Linear Surgical Stapler

Figure 2:
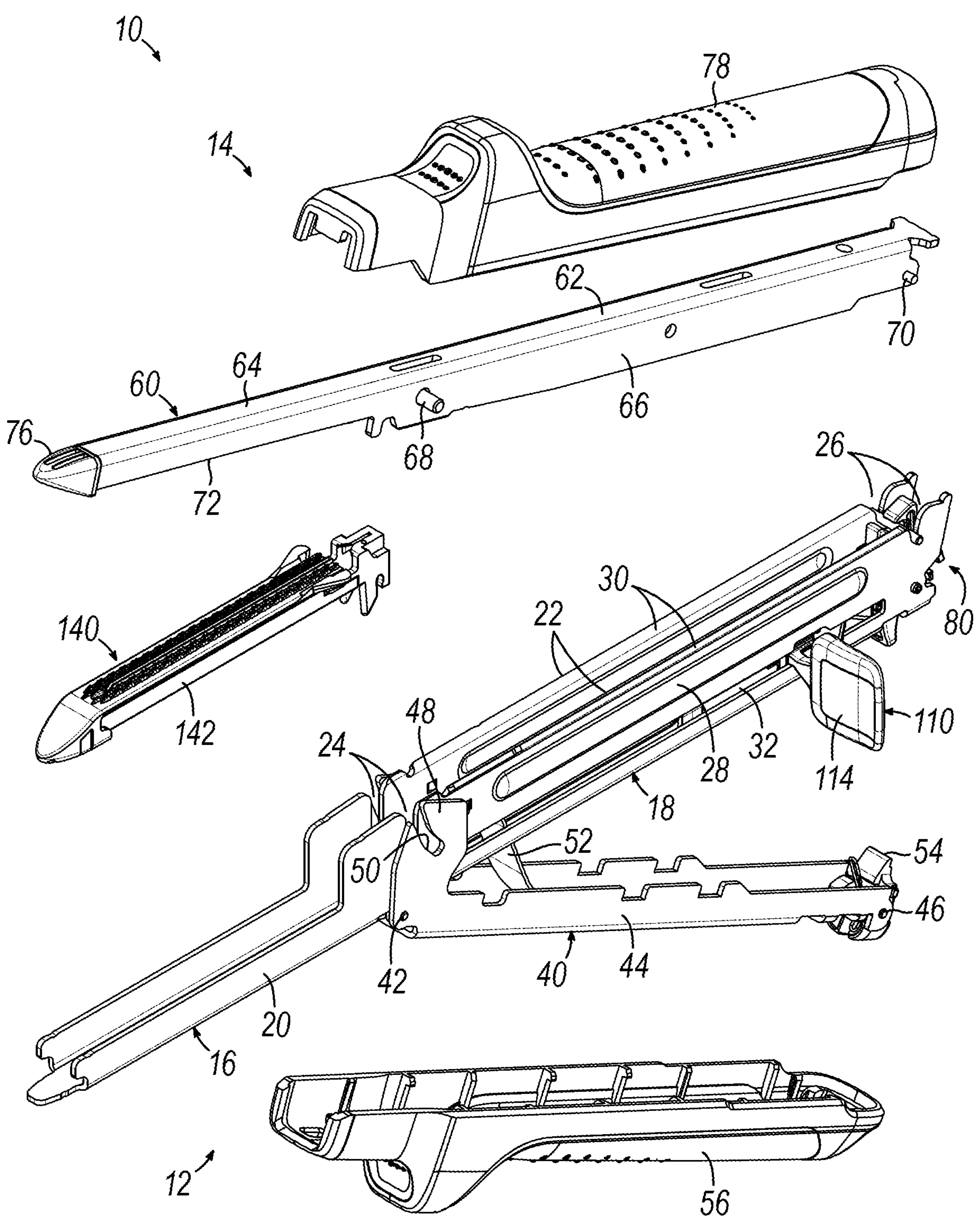
FIG. 2 depicts an exploded perspective view of the linear surgical stapler of FIG. 1, additionally showing a staple cartridge.

FIGS. 1-2 show an illustrative linear surgical stapler (10) (also referred to as a "linear cutter") suitable for use in a variety of cutting and stapling procedures, such as a gastro-intestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue. Linear surgical stapler (10) may be further configured in accordance with the teachings of U.S. patent application Ser. No. 18/316,635, entitled "Linear Surgical Stapler," filed on May 12, 2023, issued as U.S. Pat. No. 12,533,136 on Jan. 27, 2026, the disclosure of which is incorporated by reference herein.

Cartridge half (12) includes a first elongate member in the form of an elongate cartridge channel (16) having a proximal cartridge frame portion (18) and a distal jaw portion (20). Proximal cartridge frame portion (18) slidably retains a firing assembly (110) and includes a laterally opposed pair of upright side flanges (22). Each side flange (22) includes a distal slot (24) arranged at a distal end thereof, and a tapered proximal notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Figure 4:
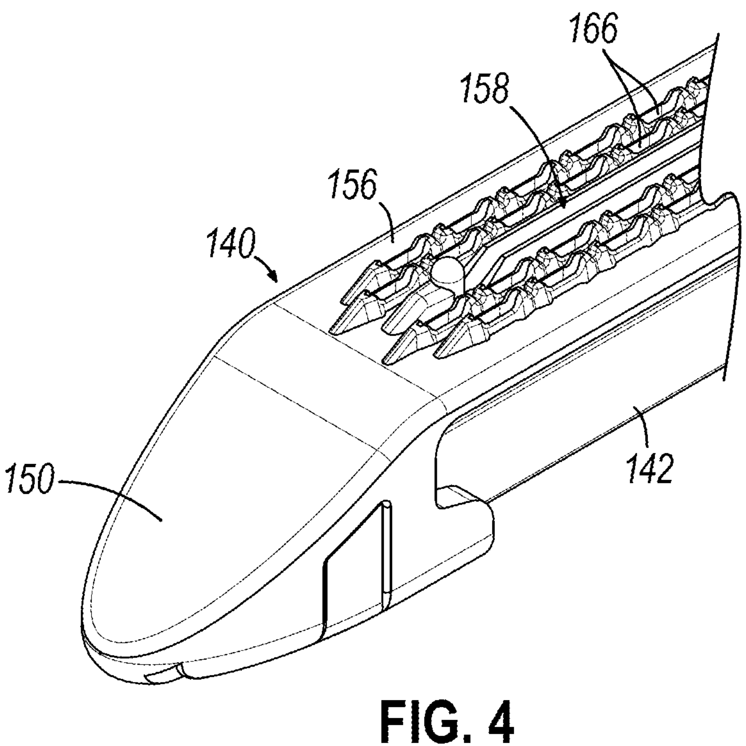
FIG. 4 depicts a perspective view of a distal end portion of the staple cartridge of FIG. 2.

Distal jaw portion (20) of cartridge channel (16) is configured to releasably receive a staple cartridge (140) (or "reload"). As shown in FIG. 4, staple cartridge (140) includes a cartridge body (142) having an upper side that defines a first stapling surface in the form of a deck (156) having a plurality of staple openings (166) that house a plurality of staples (not shown) and corresponding staple drivers (not shown).

Cartridge half (12) further includes a clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 9A:
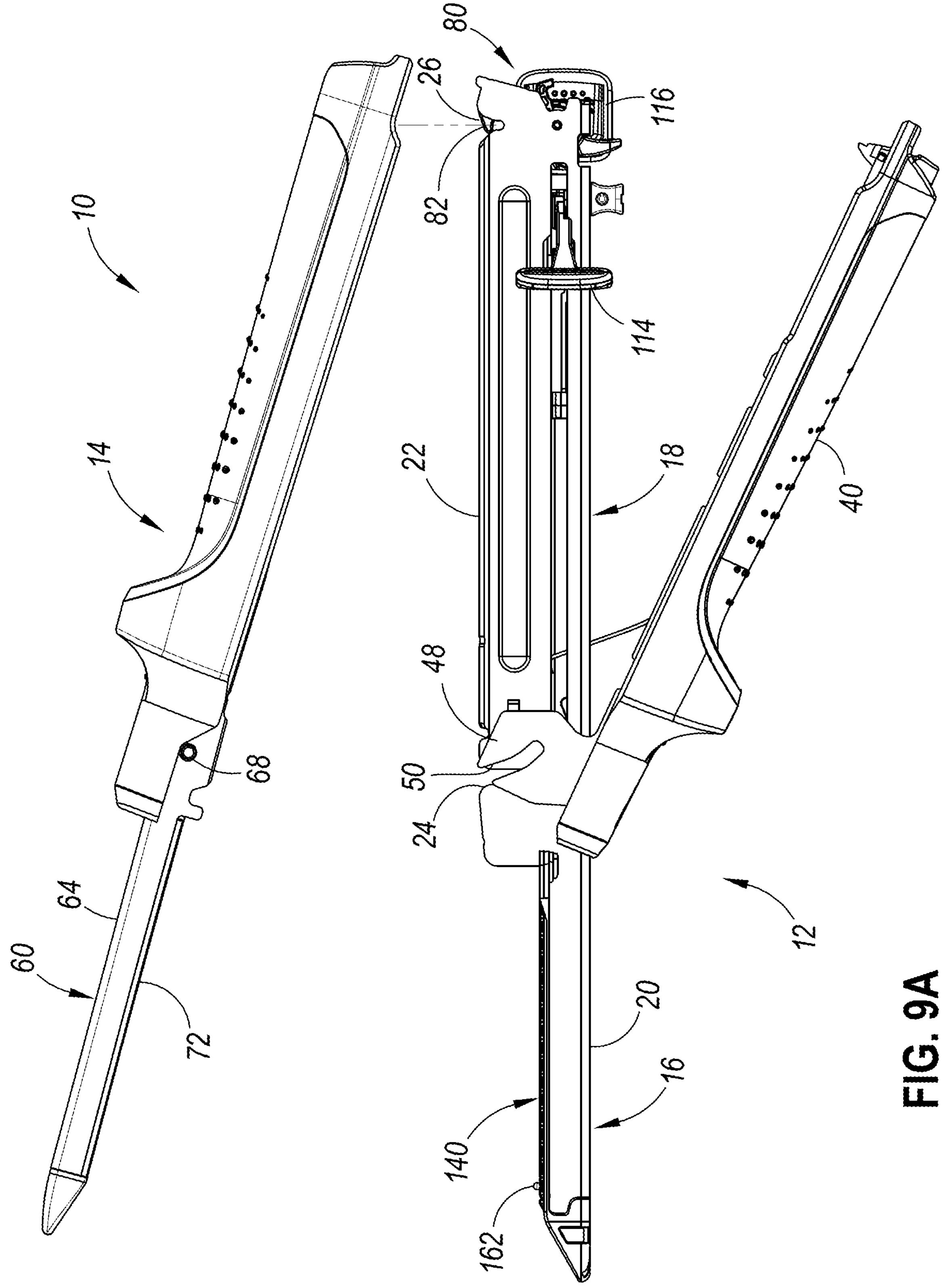
FIG. 9A depicts a side elevational view of the linear surgical stapler of FIG. 1, showing the stapler halves separated from one another with the clamp lever in the open position.
Figure 9B:
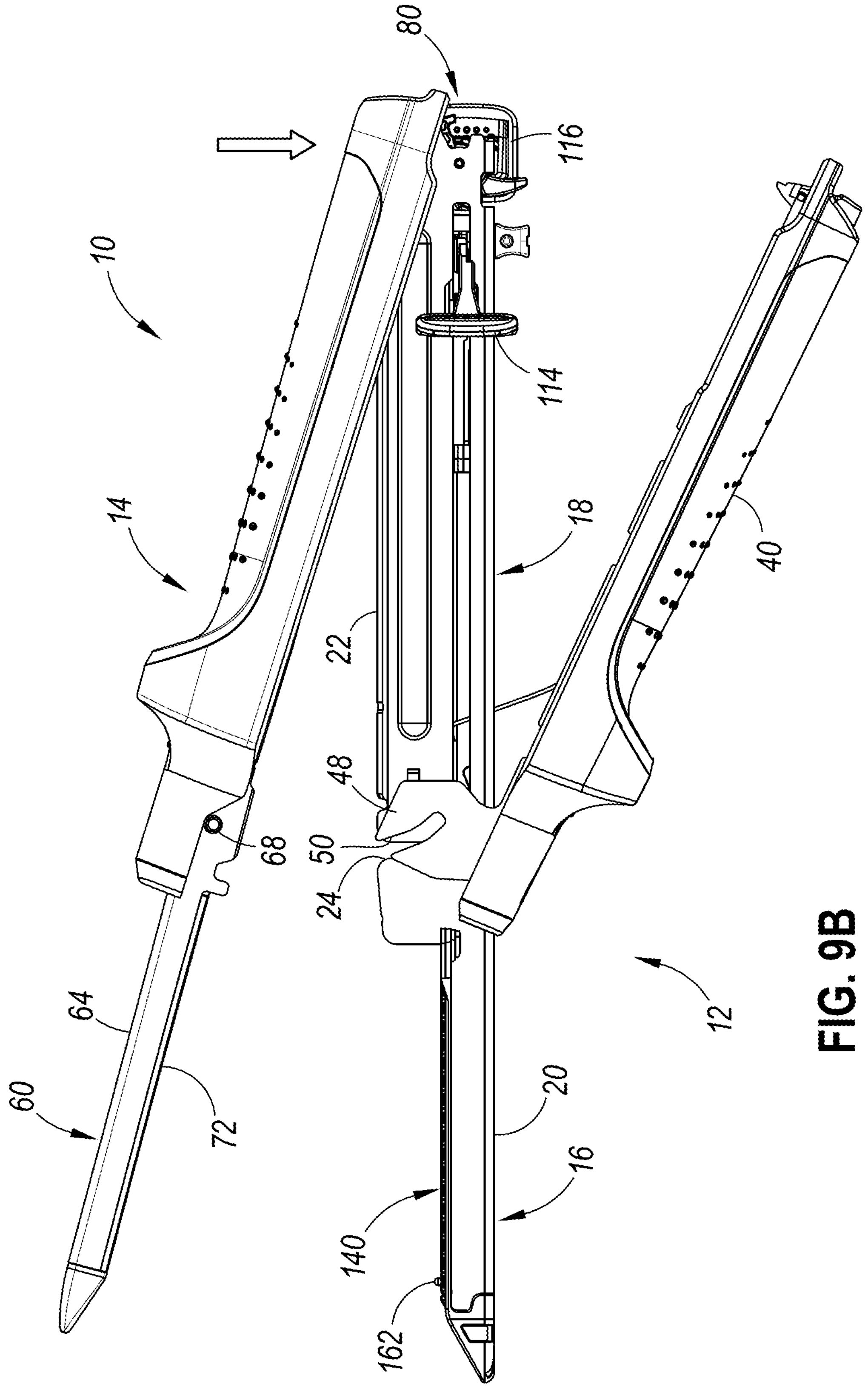
FIG. 9B depicts a side elevational view of the linear surgical stapler of FIG. 1, showing proximal ends of the stapler halves coupled together while the clamp lever is in the open position to provide the stapler in a "hang-open" state.
Figure 9C:
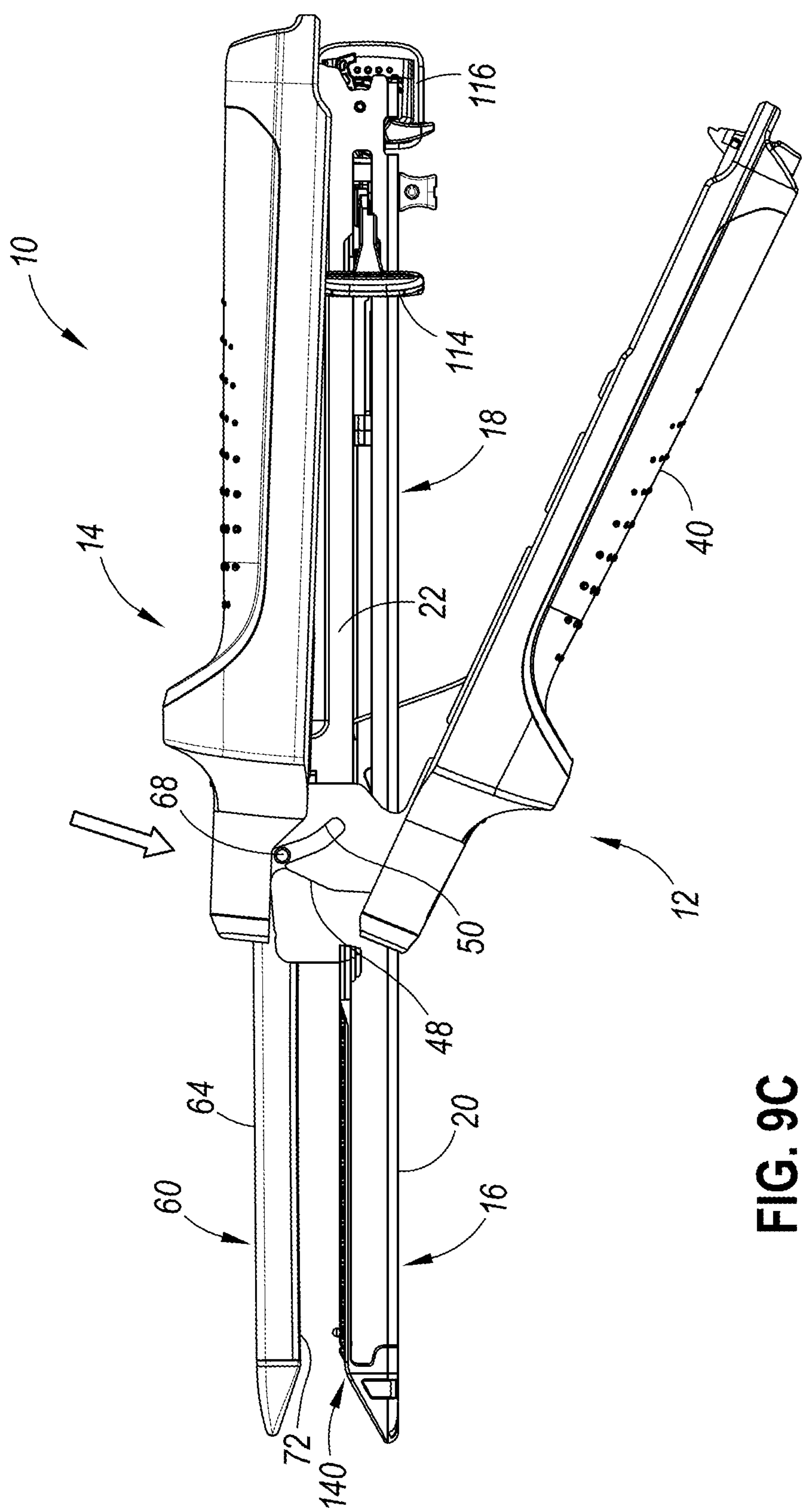
FIG. 9C depicts a side elevational view of the linear surgical stapler of FIG. 1, showing distal portions of the stapler halves having been approximated so that a distal pin of the anvil half is received by clamp lever jaws of the cartridge half.
Figure 9D:
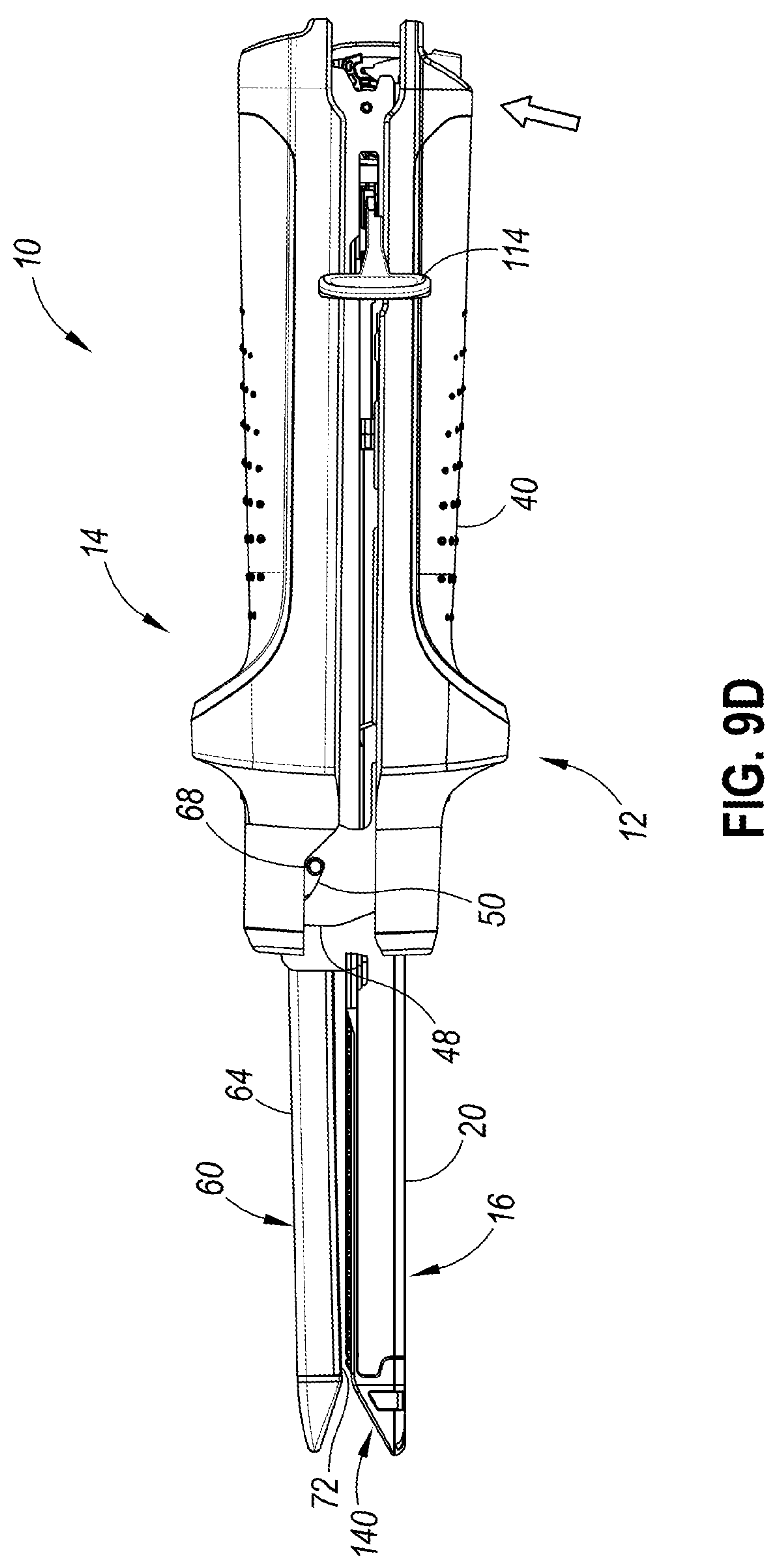
FIG. 9D depicts a side elevational view of the linear surgical stapler of FIG. 1, showing closure of the clamp lever to fully clamp the stapler halves together.

Clamp lever (40) is operable to pivot relative to cartridge channel (16) between an open position in which proximal end (46) of lever arm (44) is spaced from cartridge channel frame portion (18) as shown in FIGS. 9A-9C described below, and a closed position in which proximal end (46) confronts cartridge channel frame portion (18) as shown in FIG. 9D described below. Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 9C-9D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein.

Anvil half (14) of linear surgical stapler (10) includes a second elongate member in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
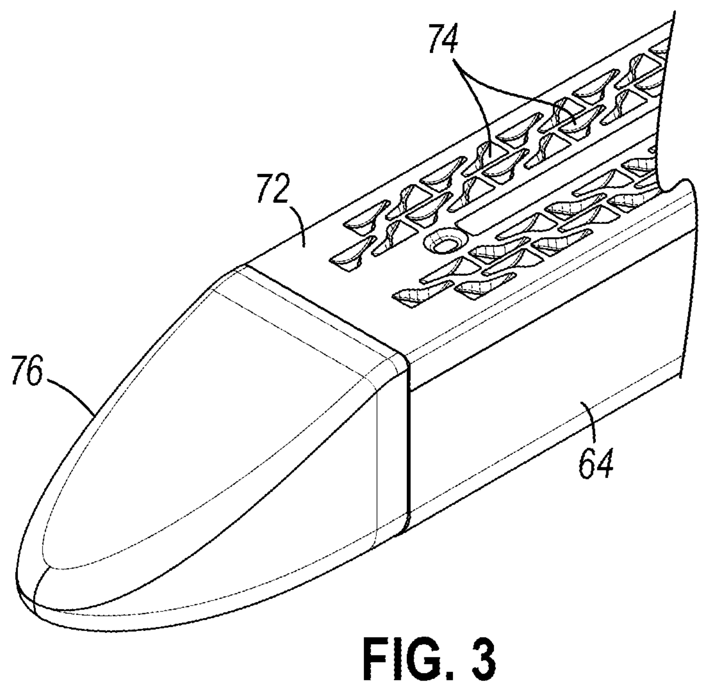
FIG. 3 depicts a perspective view of a distal end portion of the anvil half of the linear surgical stapler of FIG. 1.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, the disclosure of which is incorporated by reference herein. Anvil channel (60), anvil plate (72), and staple forming pockets (74) may be formed in one or more of the manners disclosed in U.S. Pat. No. 11,229,433; U.S. Pat. No. 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. Shrouds (56,78) include a pair of protrusions (13,15) that extend outwardly from the respective shrouds (56,78). Pair of protrusions (13,15) create a larger exterior profile than the remaining portion of shrouds (56,78). In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal cartridge frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal cartridge frame portion (18) of cartridge channel (16) at a location distal to lower release button (92) and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
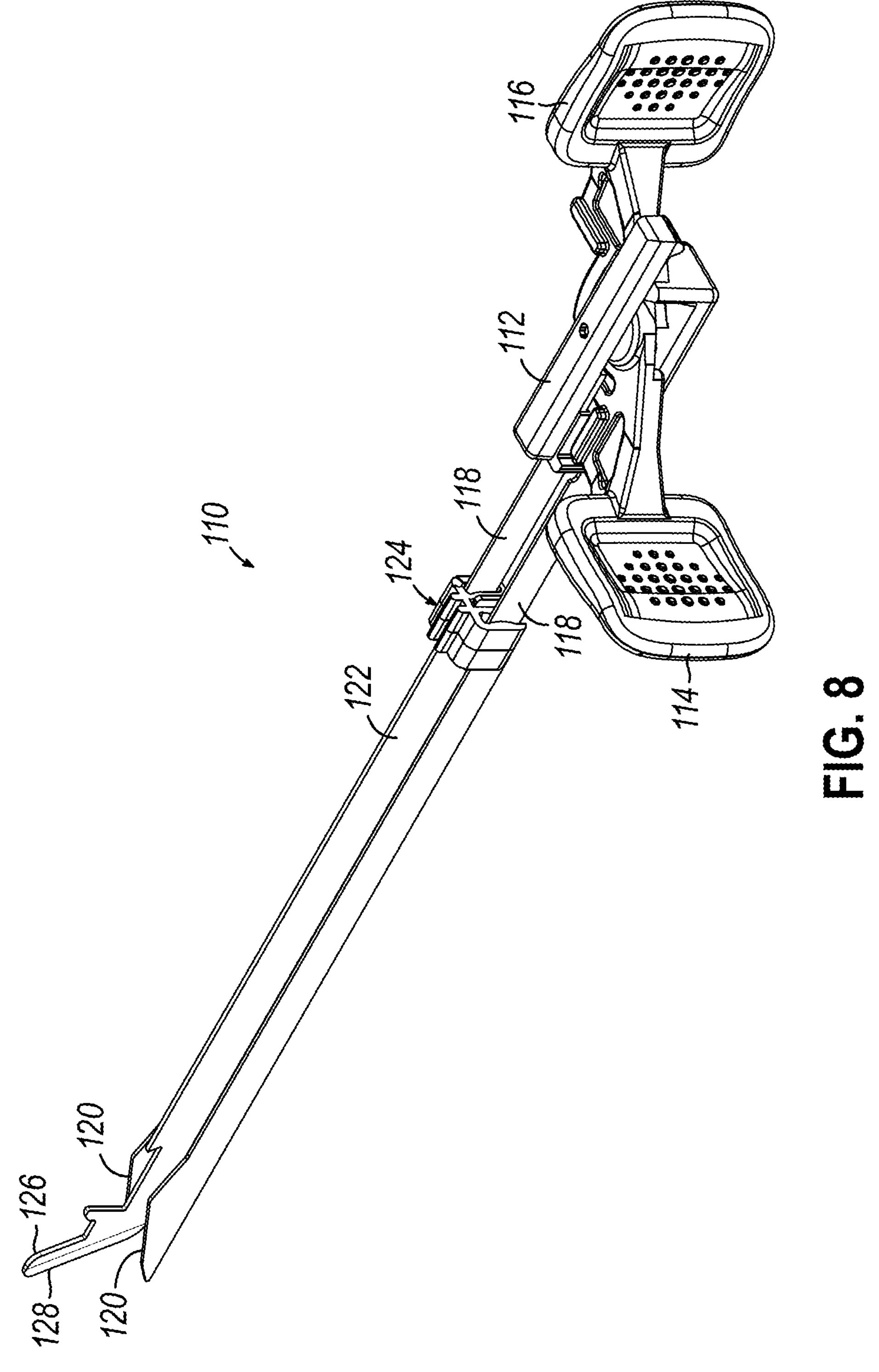
FIG. 8 depicts a perspective view of the firing assembly of FIG. 5.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (not shown) housed within staple cartridge (140) and actuate staple drivers upwardly to thereby drive (or "fire") staples from cartridge (130) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be manually deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Use of Linear Surgical Stapler

Figure 5:
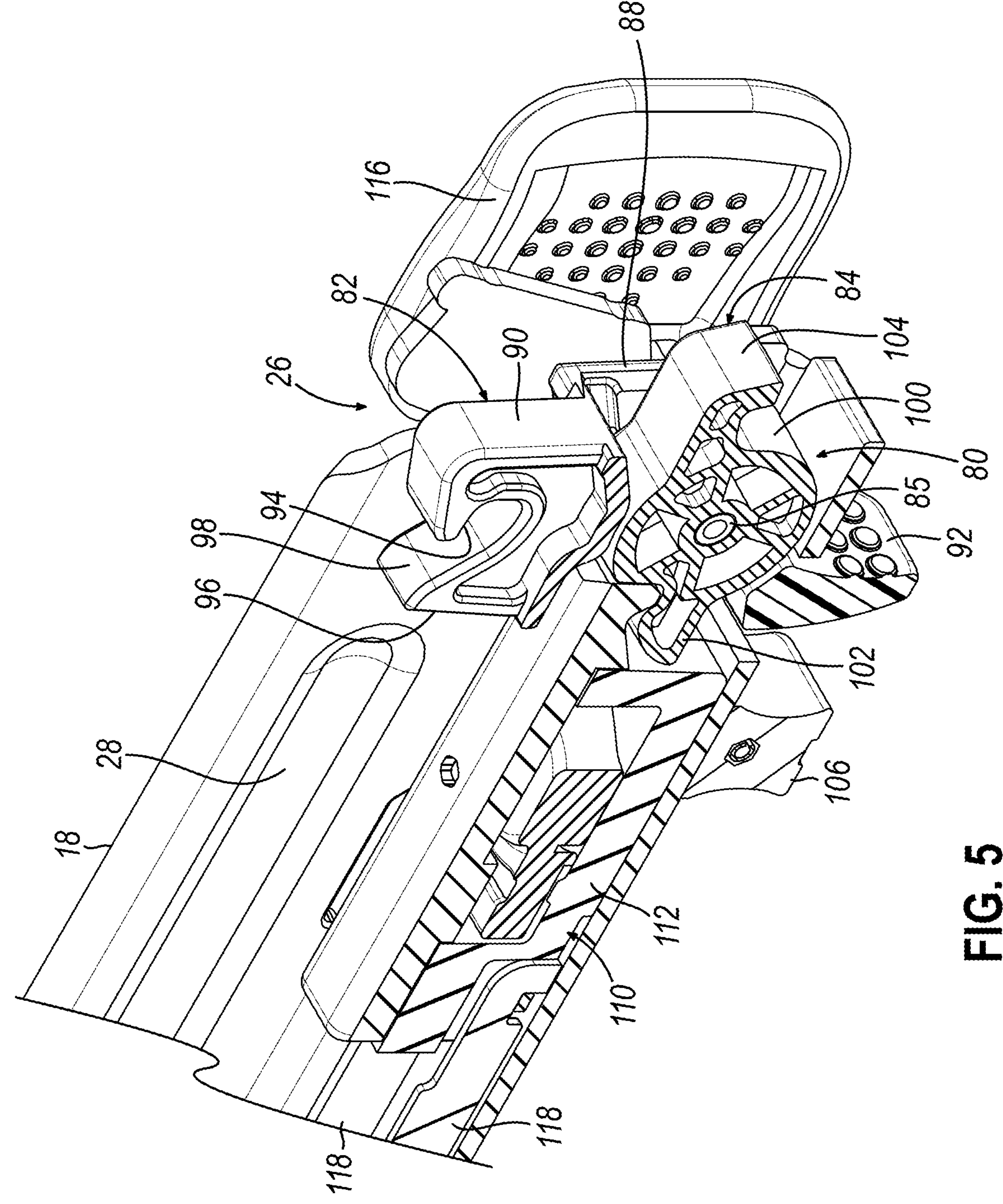
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.
Figure 6:
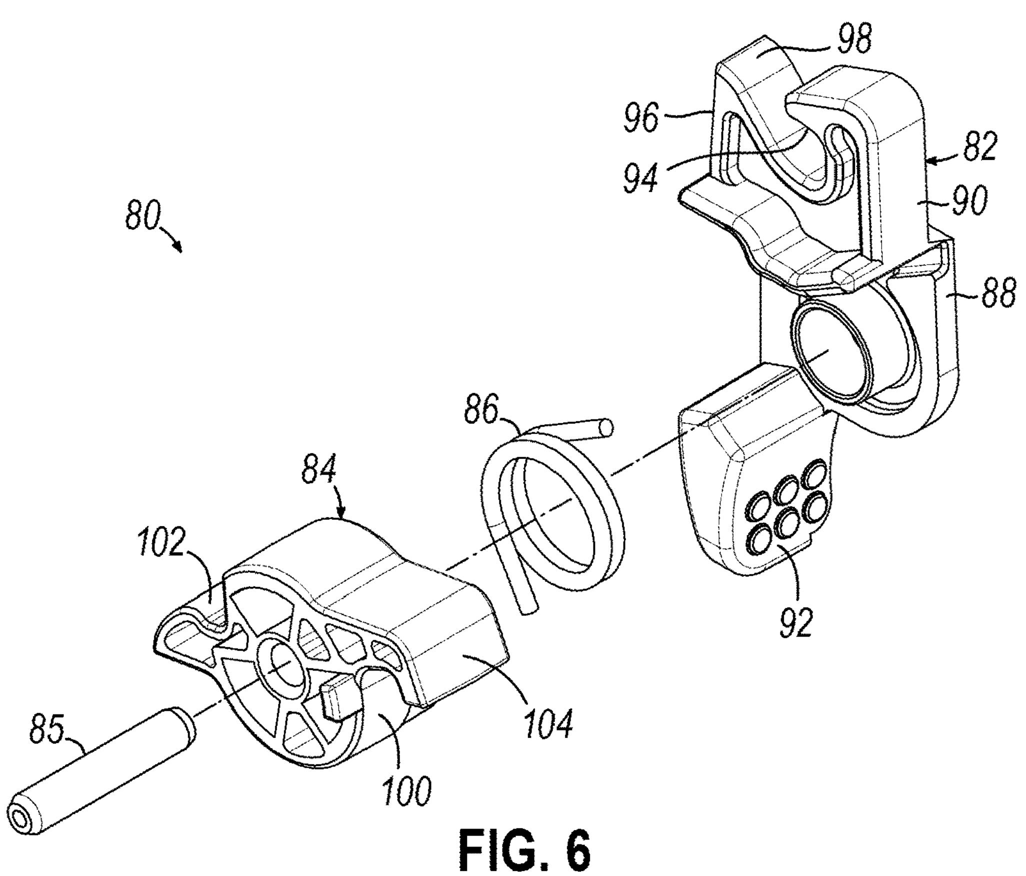
FIG. 6 depicts an exploded perspective view of the retaining assembly of FIG. 5.
Figure 7:
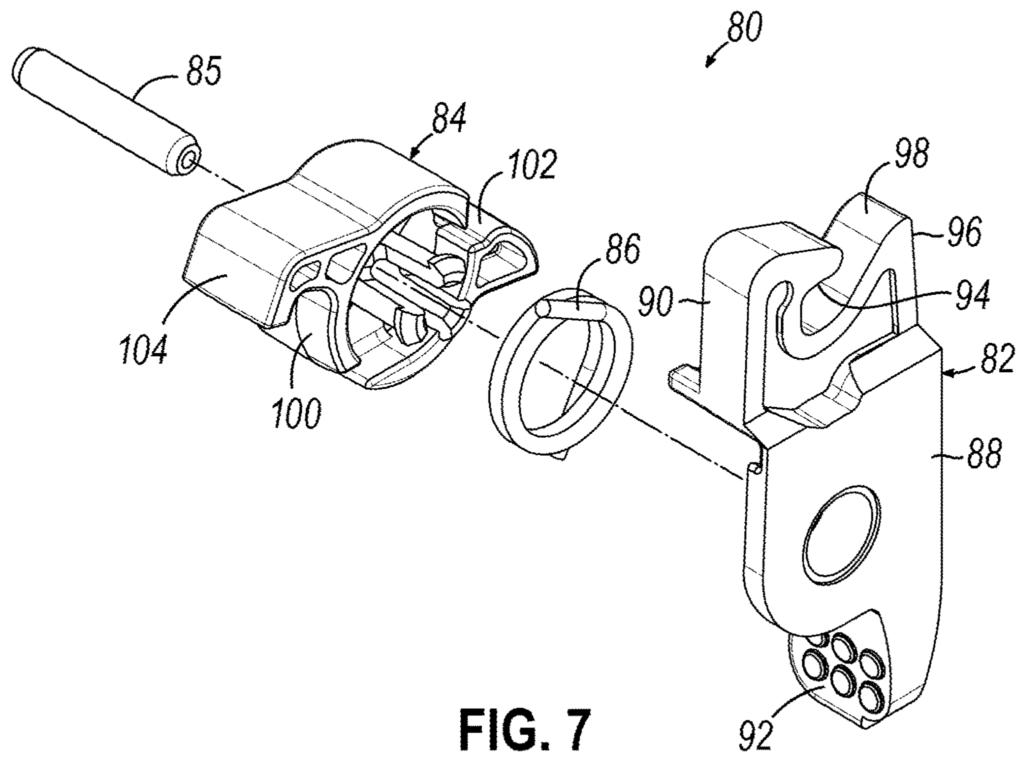
FIG. 7 depicts another exploded perspective view of the retaining assembly of FIG. 5.

FIGS. 9A-9E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with distal slots (24) of cartridge channel side flanges (22). Additionally, firing assembly (110) is maintained in its proximal home position by detent member (84) (see FIG. 5) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 9A-9B, the proximal ends of stapler halves (12, 14) are aligned with one another, and proximal anvil pin (70) (see FIG. 2) is directed downwardly into proximal tapered notches (26) of cartridge channel (16) to engage latch finger (90) (see FIG. 5) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 9B. With clamp lever (40) still in the open position as shown in FIG. 9B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into distal slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

As shown in FIG. 9D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) (see FIG. 9A) and anvil plate (72) (see FIG. 9A). A slight transverse gap is defined between staple cartridge (140) and anvil plate (72) by a tissue gap post (162) (see FIG. 9A) of staple cartridge (140), thus accommodating the tissue therebetween with a predetermined degree of tissue compression. As shown in FIGS. 9A and 9B, tissue gap post (162) is disposed at a distal end of staple cartridge (140) and is configured to contact a distal end of anvil plate (72) when stapler (10) is in the fully clamped state shown in FIG. 9D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

Figure 9E:
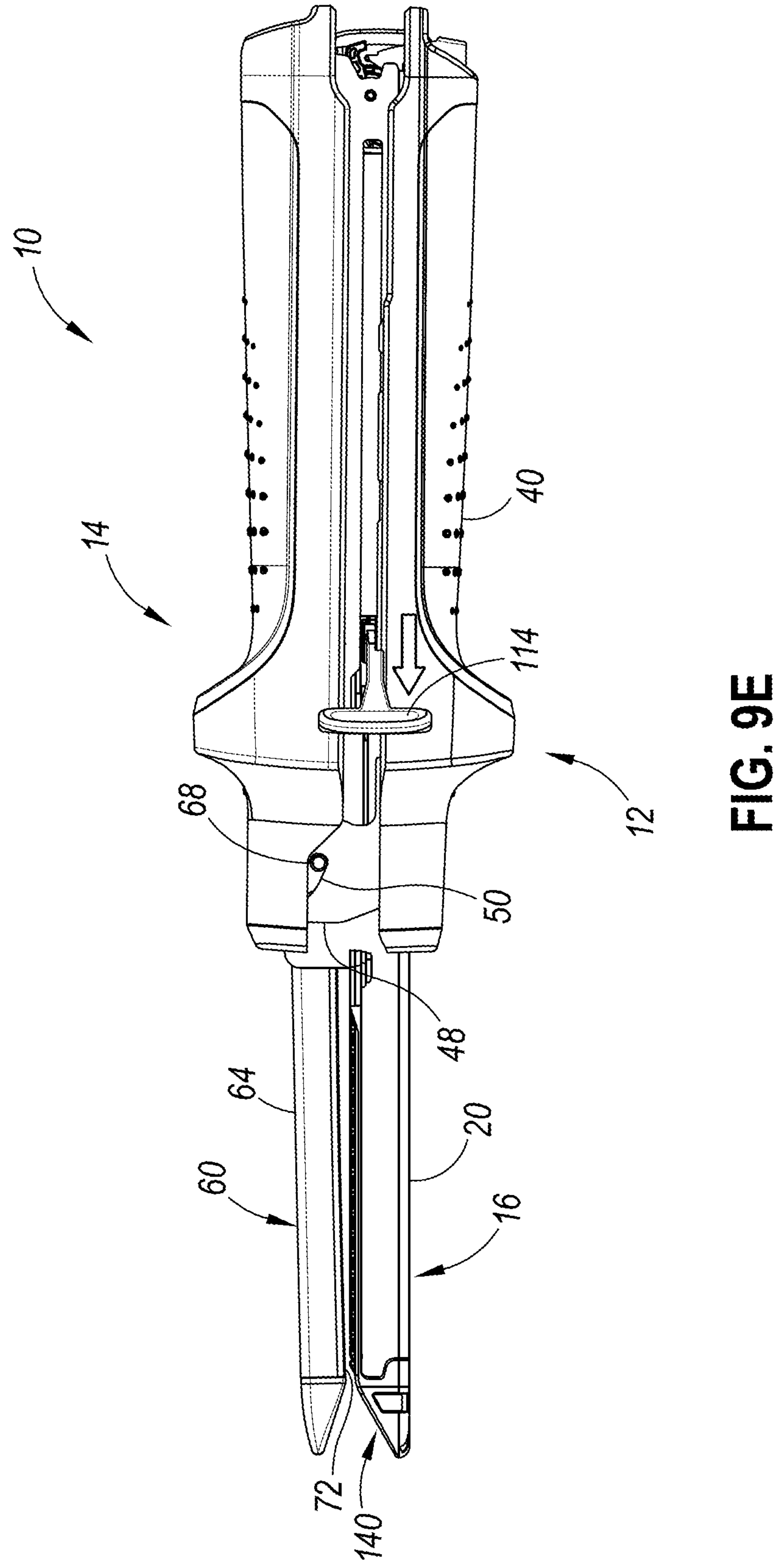
FIG. 9E depicts a side elevational view of the linear surgical stapler of FIG. 1, showing distal actuation of the firing assembly while the stapler halves are in the fully clamped state.
Figure 10:
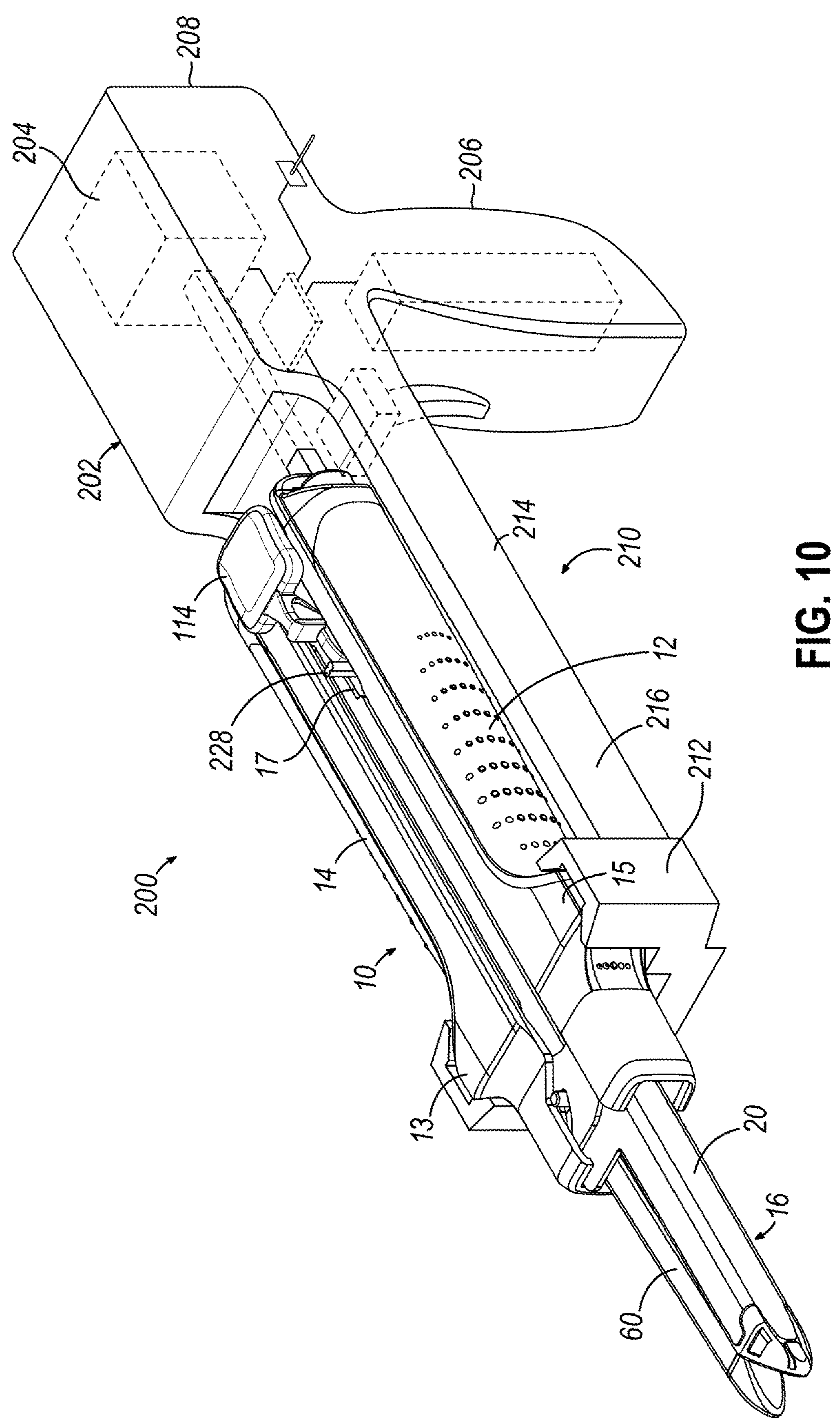
FIG. 10 depicts a perspective view of a powered surgical firing assembly including a powered firing platform fitted with the linear surgical stapler of FIG. 1.

As shown in FIG. 9E, upon reaching the fully clamped state, stapler (10) may be fired by driving a deployed actuator (114, 116) (see FIG. 9A) of firing assembly (110) distally along proximal cartridge frame portion (18) (see FIG. 9A) of cartridge half (12). This action causes elongate beams (118, 122) (see FIG. 8) of firing assembly (110) to translate distally through corresponding channels formed in staple cartridge (140) and thereby fire staples into the clamped tissue, and simultaneously cut the clamped tissue with knife member (126) (see FIG. 8). Following completion of the firing stroke, the firing assembly (110) is returned to its proximal home position via the actuator (114, 116). Clamp lever latch member (54) (see FIG. 2) may then be depressed to release the proximal end of clamp lever (40) from cartridge channel (16), thus permitting clamp lever (40) to be re-opened. Then, release button (92) (see FIG. 5) of retaining assembly (80) (see FIG. 9A) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033,266, incorporated by reference above.

II. Illustrative Powered Firing Platform

In some instances, it may be difficult for a user to manually apply sufficient distal force to actuator (114) to fire linear surgical stapler (10) and thereby cut and simultaneously staple the clamped layers of tissue. It may therefore be advantageous to provide a device that can mechanically assist a user in firing linear surgical stapler (10).

A. Overview of Powered Surgical Firing Platform

FIGS. 10-12B show an illustrative powered surgical firing assembly (200) including a powered firing platform (202) fitted with linear surgical stapler (10) described above. It should be noted that powered firing platform (202) may be backwards integrated with an existing linear surgical stapler (10) without any modification to linear surgical stapler (10). Powered firing platform (202) is configured to provide a mechanical advantage for a user through the use of a drive assembly (204) that utilizes electricity or pneumatics to provide powered firing of linear surgical stapler (10), which is otherwise fired manually by a user. Powered firing platform (202) provides the advantage that linear surgical stapler (10) may be removed from powered firing platform (202) without any tools at any time for manual firing of linear surgical stapler (10). In some instances, linear surgical stapler (10) may need to be quickly removed from powered firing platform (202) and fired manually. Powered firing platform (202) enables a user of lesser strength to provide sufficient uninterrupted force to firing assembly (110) of linear surgical stapler (10) and thereby complete a firing stroke. Powered firing platform (202) may be a disposable or reusable component that may be sterilized and used again with a disposable linear surgical stapler (10).

Powered firing platform (202) includes a body having a handle (206), a housing (208), and an elongate support (210), and a drive assembly (204) supported by body.

Powered firing platform (202) is constructed of one or more surgically safe materials such as plastic, metal, or other materials known in the art to be surgically safe and have suitably rigid properties. Handle (206) is configured to be gripped by a user. As shown, handle (206) is obliquely positioned relative to linear surgical stapler (10). More specifically, handle (206) extends downwardly from and depends downwardly from a medial portion of housing (208). In some versions handle (206) may also be aligned with elongate support (210) and affixed to a proximal portion of housing (208) to provide a powered firing platform (202) including a lesser cross-sectional area for additional access to surgical sites of the patient's body. Housing (208) is configured to provide a mechanical ground and liquid tight enclosure for drive assembly (204). Housing (208) also acts as a mechanical ground for elongate support (210) that extends distally away from housing (208). Housing (208), handle (206), and elongate support (210) may be blown molded or manufactured through additive manufacturing in two pieces that may be snap fit together or secured with fasteners (not shown). Additionally, housing (208), handle (206), and elongate support (210) may be blow molded or manufactured through additive manufacturing in a single piece. In yet other versions, housing (208), handle (206), and elongate support (210) may be manufactured through molding or additive manufacturing in multiple pieces that are subsequently assembled to provide access for service or repair or so that portions of powered firing platform (202) may be disposed of, and other portions may be sterilized and reused. By way of example only, handle (206) and housing (208) may be reused whereas elongate support (210) may be disposed and replaced.

Elongate support (210) includes a proximal portion affixed to a distal portion of housing (208). Elongate support (210) includes an elongate member (214) that extends distally to a cradle (212). Cradle (212) is positioned on distal end of elongate member (214). Elongate member (214) includes a guideway (218), a guide channel (220), and a pair of outer rails (216). Guideway (218) includes a generally planar shape and is configured to mate with a side surface of linear surgical stapler (10). In some versions, guideway (218) may be contoured to complement a side surface of linear surgical stapler (10). Guide channel (220) is defined on two sides by guideway (218) and includes a rectangular shape. Guide channel (220) is sized and shaped to movably support a portion of drive assembly (204). In some versions, guide channel (220) may be shaped to prevent portion of drive assembly (204) from deviating from side to side. In such versions, guide channel (220) may include a "T" or an "I" shape or another shape known by one of ordinary skill in the art to maintain a driver along a longitudinal axis. Pair of outer rails (216) extend generally parallel to the support longitudinal axis and complement exterior profile of stapler halves (12,14). Pair of outer rails (216) may also include a taper (not shown) to aid in longitudinally locating exterior profile of stapler halves (12,14). Pair of outer rails (216) may also include foam or rubber (not shown) positioned on an interior surface of each of outer rails (216). Foam or rubber is configured to frictionally engage exterior of stapler platform (202) when powered firing platform (202) is navigated to a surgical site. Powered firing platform (202) may be required to be inverted or rotated to reach a surgical site. Cradle (212) aids in securing linear surgical stapler (10) within powered firing platform (202).

Cradle (212) includes a pair of C shaped members (222) obliquely extending from elongate member (214). Each C shaped member (222) is sized and configured to longitudinally locate surgical linear stapler (10) about a distal portion of exterior profile of stapler halves (12,14). C shaped members (222) may be resiliently biased towards the support longitudinal axis. Each C shaped member (222) includes a planar portion (224) and a pair of angled portions (226) configured to grasp a pair of protrusions (13,15) that extend from each of stapler halves (12,14). Cradle may additionally include a foam, or a rubber configured to frictionally engage protrusions (13,15) that extend from pair of C shaped members (222).

In some versions, elongate support (210) is clocked 90 degrees where it is affixed to distal end of housing (208). Cradle (212) is configured to orientate anvil above or below the support linear surgical stapler (10), rather than to either side of the linear surgical stapler (10). In such a version pin (228) is obliquely positioned relative to handle (206). This version may include features incorporated into cradle (212) or pair of outer rails (216) that complement exterior profile of linear surgical stapler (10) so that linear surgical stapler (10) may only be placed into powered firing platform (202) in one orientation.

Drive assembly (204) includes an actuator (230), a forward circuit (232), a reverse circuit (234), and a driver (236). In the present version drive assembly (204) utilizes electricity to provide a mechanical advantage to the user to ease the force needed to be input by a user to fire firing assembly (110). Both forward and reverse circuits (232, 234) include wiring (238) configured to carry a current between components of circuits (232, 234). Forward circuit (232) includes a forward control circuit (240) and a forward main circuit (242). Forward control circuit (240) includes an initiation device (244) and wiring (238). Initiation device (244) has a trigger (246) and a forward switch (248). Trigger (246) is rotatably coupled within housing (208) and/or handle (206). Trigger (246) is configured to be manipulated by a user from a distal position to a proximal position to activate forward switch (248). Trigger (246) may include a spring (not shown) configured to return trigger (246) from proximal position to distal position after interacting with forward switch (248). Forward switch (248) is a momentary push button that includes an open position and a closed position. Forward switch (248) in an unactivated state is in normally open position and closed position in activated state. Forward control circuit (240) actuates forward relay (250) via forward switch (248) and wiring (238).

Forward main circuit (242) includes forward relay (250) and wiring (238). Forward relay (250) may be in the form of a conventional electromagnetic relay, a transistor, or another device known in the art to allow a main circuit to provide voltage to an actuator from a control circuit. Forward relay (250) includes an unactuated state and an actuated state. In actuated state forward relay (250) connects power supply (252) to actuator (230) via wiring (238). Forward relay (250) provides actuator (230) a voltage having a first polarity.

Power supply (252) in the present version includes a battery (254). Battery (254) may be of the disposable or rechargeable type. Battery (254) may include alkaline, lithium ion, or other batteries known in the art to provide a compact source of energy. In other versions, battery (254) may be omitted and powered firing platform (202) may instead be powered by an external power supply (not shown) In these versions, voltage is supplied by a connector (not shown) and a cord (not shown) configured to connect with a standard wall outlet or with an external battery or other external power supply unit.

Reverse circuit (234) includes a reverse control circuit (256), a reverse main circuit (258). It should be noted that reverse circuit (234) may utilize a portion of wiring of forward circuit (232) and are not mutually exclusive of each other. In some instances, the forward and reverse components may include the same components configured to reverse the flow of electrons. Reverse control circuit (234) includes a reverse switch (260) and wiring (238), and reverse main circuit (258) includes a reverse relay (262) and wiring (238). Reverse control circuit (234) provides power to actuate the reverse relay (262) that electrically connects power supply (252) with reverse relay (262). Reverse switch (260) may be located anywhere upon the handle (206) or housing (208). Reverse switch (260) may include a safety feature configured to prevent inadvertent activation of the reverse switch (260). Reverse switch (260) may also be incorporated into forward switch (248) or trigger (246). Reverse main circuit (258) includes reverse relay (262) that interconnects battery (254) with actuator (230) to supply a voltage having a second polarity opposite the first polarity.

Actuator (230) may include a motor (264) and a transmission (266) as shown in the present version. In other versions, motor (264) may be substituted with an electrical solenoid (not shown). Motor (264) is configured to be supplied with voltage via a forward or reverse relay (250, 262). Motor (264) is rotationally connected with transmission (266). Transmission (266) may include one or more gears that interconnect motor (264) to driver (236). Transmission (266) is configured to change the gearing of motor to provide additional speed or torque to actuate driver (236). Motor (264) is configured to rotate in a first direction when supplied by voltage with a first polarity and in a second direction, opposite first direction when supplied voltage with a second polarity.

Driver (236) includes a rack (268), an elongate rod (270), and an engagement feature (272). Rack (268) may include a plurality of linear gear teeth configured to mesh with a rotational gear of transmission (266). Rack (268) is configured to take the rotational force supplied by transmission (266) and convert that rotational motion into a linear motion that drives elongate rod (270) either distally when motor (264) rotates in a first direction or proximally when motor (264) rotates in a second direction. Rack (268) may also include a lead screw (not shown), or any other device known in the art to convert a rotational motion into a linear motion. Elongate rod (270) may be integrally formed with rack (268) and extends distally to engagement feature (272). Engagement feature (272) is positioned on a distal end of elongate rod (270 and is configured to mate with a portion of firing assembly (110) and slidably translate along guide channel (220). In the present version, engagement feature (272) includes a block (274), a guide (276), and a protrusion shown in the form of an elongate pin (228). Guide (276) includes a shape that complements the shape of guide channel (220). As shown, guide (276) includes a rectangular shape and is configured to slidably translate within guide channel (220). Pin (228) extends transversely away from block (274) and is configured to be inserted at least partially through or otherwise mate with a portion of firing assembly (110) of linear surgical stapler (10). In the present version, pin (228) fits within a pin aperture (17) that is defined by firing assembly (110). Pin (228) is configured to engage firing assembly (110) to translate firing assembly (110) distally or proximally.

In other versions, in place of or in addition to pin (228), engagement feature (272) may include a slot, channel, recess, or other opening-type feature that is sized and shaped to receive and releasably retain a protruding structure of firing assembly (110), such as a deployed firing actuator (114, 116), for example. Furthermore, it will be appreciated that while powered firing platform (202) of the present version is shown and described herein in connection with linear surgical stapler (10), powered firing platform (202) of other versions may be alternatively configured to receive and engage the firing assembly of various other types of linear surgical staplers.

In other versions, actuator (230) may incorporate pneumatics in place of electric motor (264). For instance, actuator (230) may be in the form of an air solenoid. Power supply (252) may include a compressed gas such as disposable CO2 tanks or service air (not shown). Service air may be supplied to powered firing platform (202) through a service air connector. Service air produced remotely in an air compressor and supplied to powered firing platform (202) through a hose. Initiation device (244) may be electrical or mechanical. Initiation device (244) either interconnects with an electrically controlled valve (not shown) located between power supply (252) and actuator (230) or includes a mechanical valve (not shown) that is directly connected to trigger (246).

Figure 11:
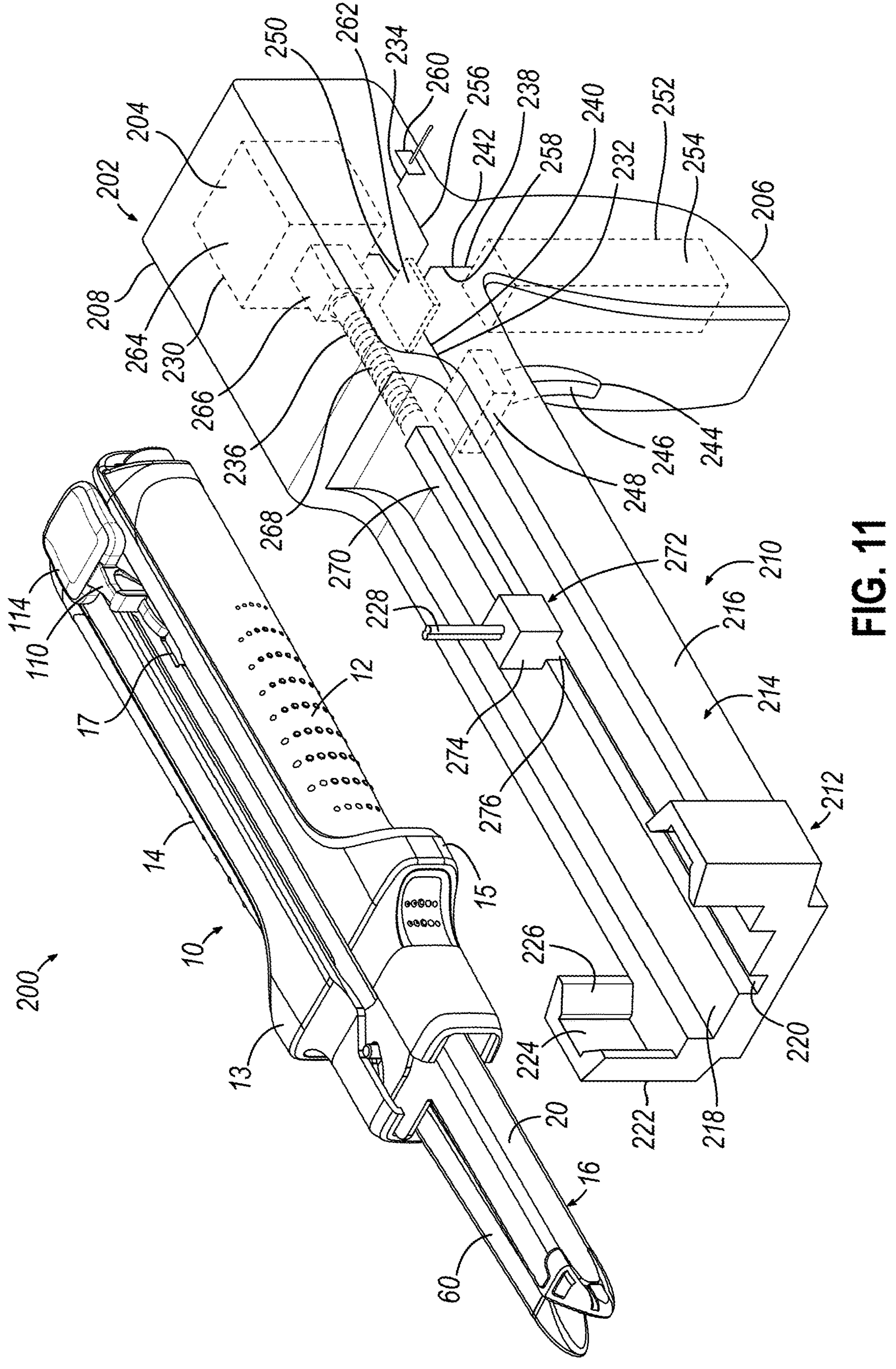
FIG. 11 depicts the powered surgical firing assembly of FIG. 10 with the powered firing platform spaced apart from the linear surgical stapler before the linear surgical stapler is fitted within the powered firing platform.

FIG. 11 shows linear surgical stapler (10) spaced apart from and aligned with powered firing platform (202). Powered firing platform (202) is provided in a retracted, unfired position with pin (228) in a proximal position. Pair of protrusions (13,15) positioned on an exterior profile of stapler halves (12,14) are aligned between pair of C shaped members (222) and the remaining exterior profile of stapler halves (12,14) is aligned with pair of outer rails (216). Additionally, pin (228) is aligned with pin aperture (280) that extends laterally through firing assembly (110) of linear surgical stapler (10). A user provides lateral force upon linear surgical stapler (10) with a first hand while providing support to powered firing platform (202) with the other hand to securely place linear surgical stapler (10) within powered firing platform (202).

Figure 12A:
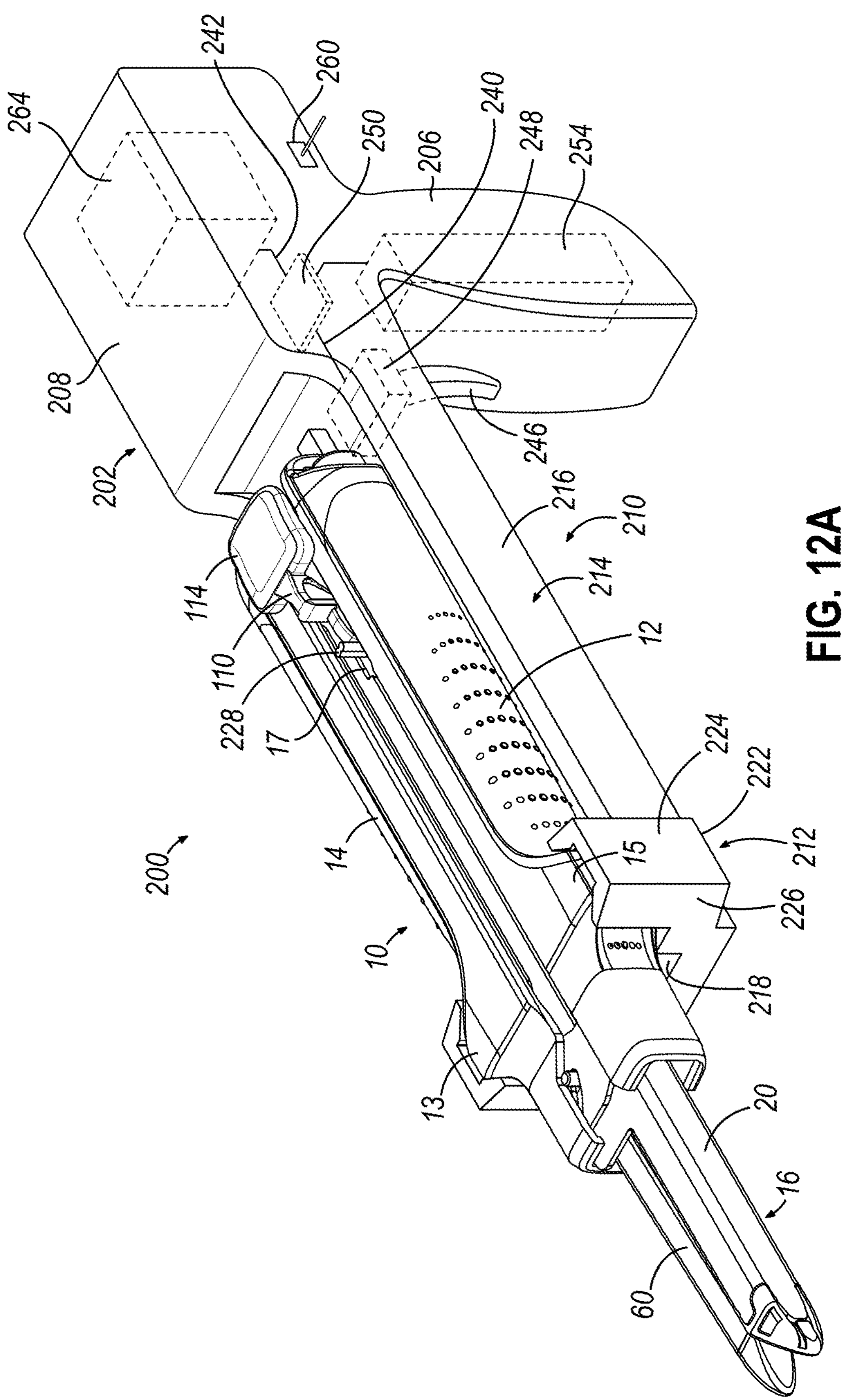
FIG. 12A depicts the powered surgical firing assembly of FIG. 10 in a retracted, unfired condition.

FIG. 12A shows powered surgical firing assembly (200) with linear surgical stapler (10) installed within powered firing platform (202) in a retracted, unfired position after a user has performed the steps shown in FIG. 9A-9D. In use, a user manually manipulates trigger (246) from a distal position to a proximal position. In the proximal position, trigger (246) engages forward switch (248) transitioning forward switch (248) from an open position to a closed position. Forward switch (248) provides voltage to forward relay (250) via forward control circuit (240). Forward relay (250) completes forward main circuit (242) thereby providing a voltage with a first polarity from battery (254) to motor (264).

Figure 12B:
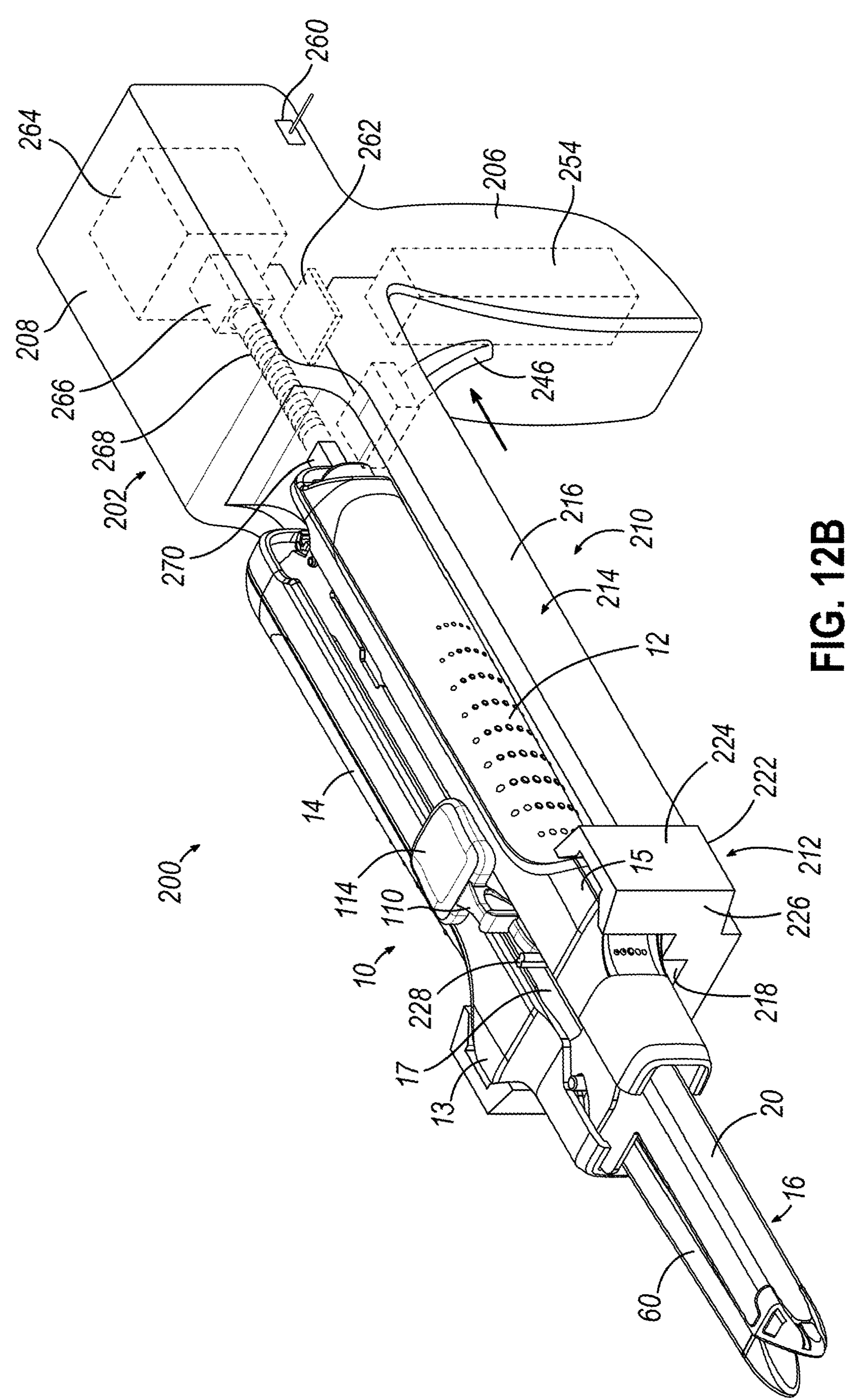
FIG. 12B depicts the powered surgical firing surgical assembly of FIG. 10 in an extended, fired condition.

FIG. 12B shows powered surgical firing assembly (200) with linear surgical stapler (10) installed within powered firing platform (202) in an extended, fired position after motor (264) has been provided a voltage with a first polarity, which rotated motor (264) in a first direction. Motor (264) rotatably engages transmission (266), which rotatably engages rack (268). Rack (268) is thereby translated distally. Rack (268) translates elongate rod (270) distally. Elongate rod (270) moves pin (228) distally, which moves firing assembly (110) of linear surgical stapler (10) distally thereby clamping down on one or more layers of tissue, cutting through the clamped layers, and simultaneously driving staples through the layers.

Powered surgical firing assembly (200) may be returned to retracted, unfired position (see FIG. 12A) by activating reverse switch (260). Reverse switch (260) supplies a voltage from battery (254) to reverse relay (262). In response to reverse switch (260) being activated, reverse relay (262)

supplies a voltage having a second polarity from battery (254) to motor (264). Motor (264) rotates in a second direction. Motor (264) rotatably engages transmission (266), which rotatably engages rack (268) thereby translating rack (268) proximally. Rack (268) translates elongate rod (270) proximally. Elongate rod (270) moves engagement feature (272) proximally, which moves firing assembly (110) of linear surgical stapler (10) proximally thereby returning linear surgical stapler (10) to retracted position. Linear surgical stapler (10) may be removed, reloaded with a new staple cartridge (140) and the steps of FIGS. 9A-9B may be performed again. Linear surgical stapler (10) may be reinstalled within powered surgical firing assembly (200) as shown in FIG. 11.

B. Illustrative Powered Firing Platform Having Data Interconnectivity

Figure 13:
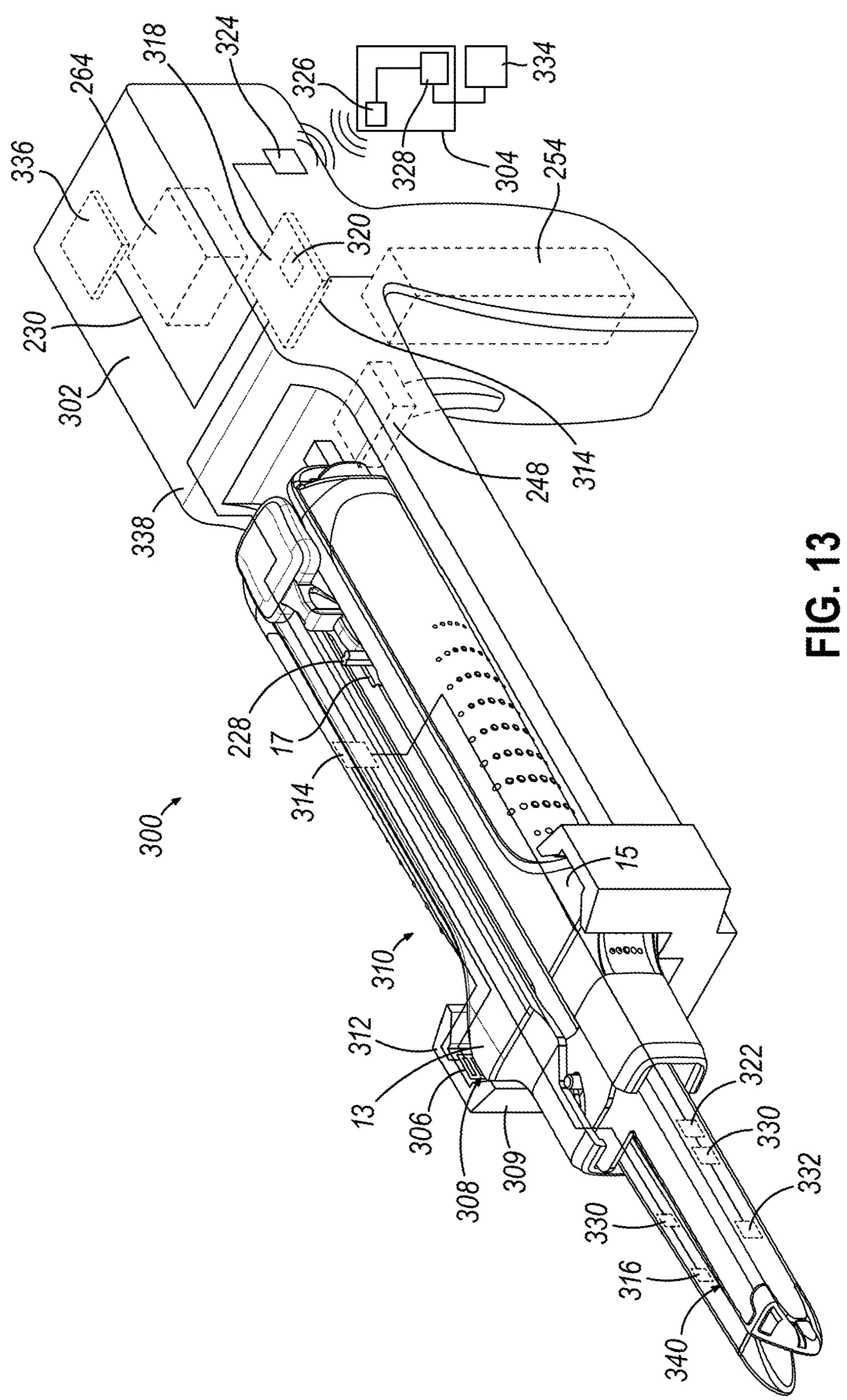
FIG. 13 depicts a perspective view of another powered surgical firing assembly including a powered firing platform having a first electrical connector and fitted with a linear surgical stapler having a second electrical connector.
Figure 14A:
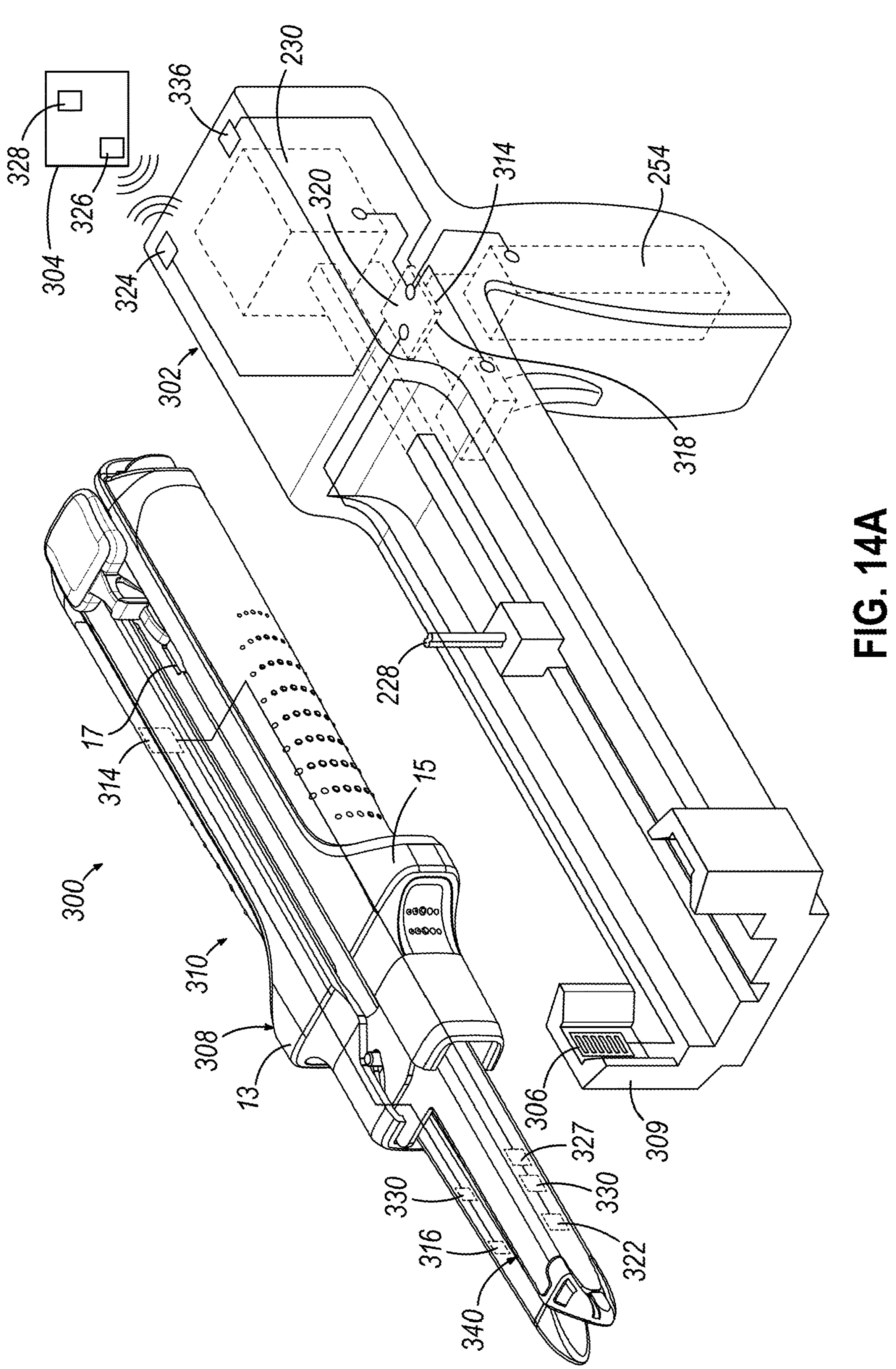
FIG. 14A depicts a perspective view of the powered surgical firing assembly of FIG. 13 with the linear surgical stapler spaced apart from the powered firing platform.
Figure 14B:
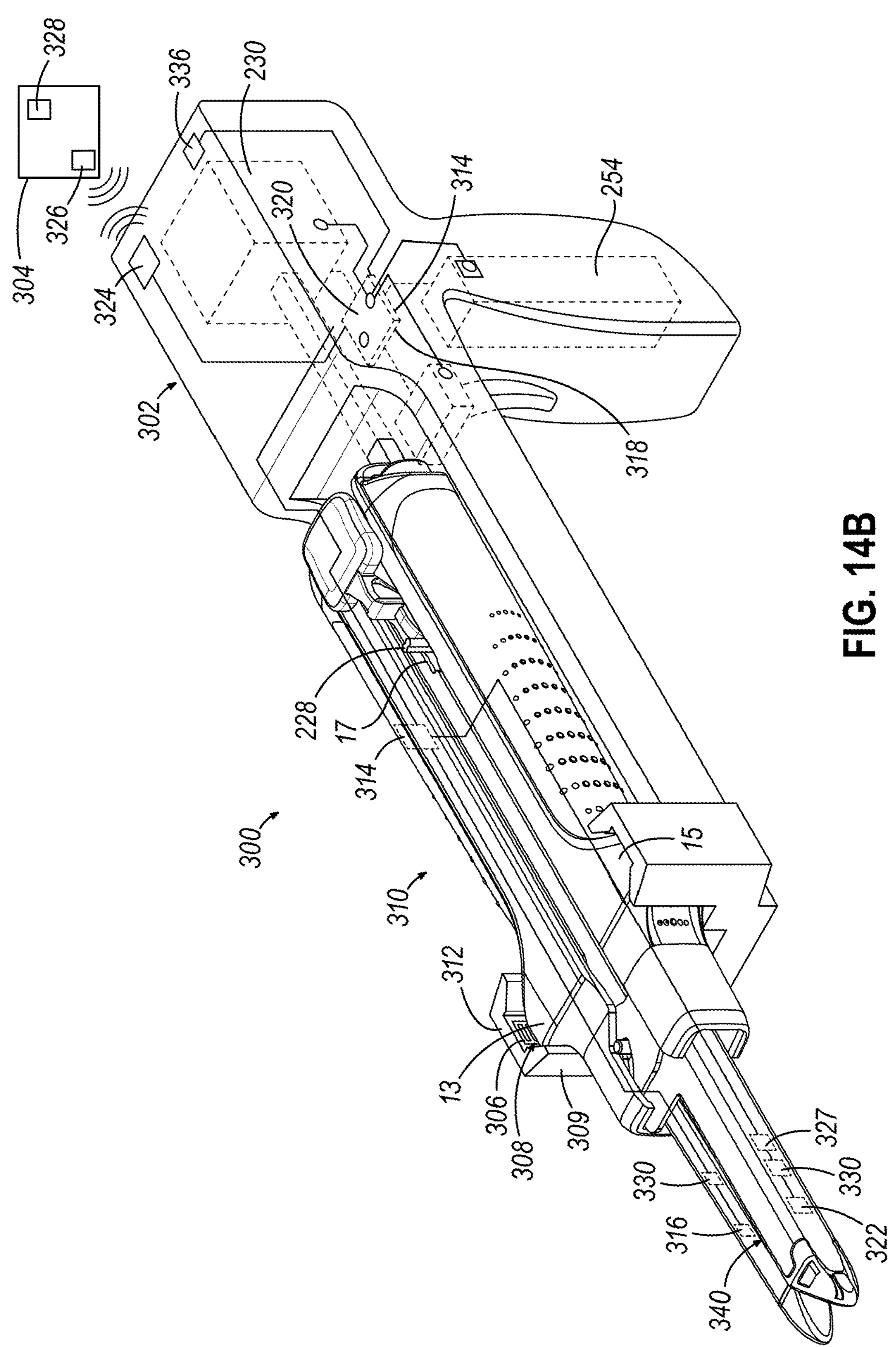
FIG. 14B depicts a perspective view of the powered surgical firing assembly of FIG. 12 with the linear surgical stapler fitted within the powered firing platform such that the first electrical connector is mated with the second electrical connector.

FIGS. 13-14B show another illustrative powered surgical firing assembly (300) fitted with a linear surgical stapler (310). Powered surgical firing assembly (300) is similar to powered surgical firing assembly (200) described above except as otherwise described below. In that regard, powered surgical firing assembly (300) includes a powered firing platform (302) and a linear surgical stapler (310) that incorporate additional features configured to provide intra-operative awareness to a user and/or the ability to send data to a remote processing unit (referred to herein as a "hub") (304). Such data may relate to operation of linear surgical stapler (310) (e.g., a firing speed of firing assembly or a firing force applied to firing assembly (110) and/or operation of powered firing platform (302). Powered surgical firing assembly (300) is usable with both linear surgical stapler (310) configured to share and utilize data, or with a conventional linear surgical stapler (10) that does not have this data sharing and utilization capability. A conventional linear surgical stapler (10) may be backwards integrated into powered firing platform (302) without any modification to linear surgical stapler (10) as shown.

Powered surgical firing assembly (300) differs from powered surgical firing assembly (200) in that powered surgical firing assembly (300) includes a first electrical connector (306) positioned upon powered firing platform (302) and a second electrical connector (308) positioned upon linear surgical stapler (310). First electrical connector (306) is configured to mate with second electrical connector (308) when linear surgical stapler (310) is positioned within powered firing platform (302). First and second connectors (306, 308) may be a pogo-pin style, a Bourns modular contact-style, or any other connector known in the art to provide an electrical connection by engaging first and second connectors (306, 308) together. As shown, first electrical connector (306) is positioned upon cradle (309) and second connector (308) is positioned upon one of protrusions (13, 15). It should be noted that first and second connectors (306, 308) when mated together form a connector assembly (312). It should be noted the placement of connector assembly (312) is merely one example of the placement of connector assembly (312), and connector assembly (312) may be placed anywhere that linear surgical stapler (310) includes a surface that engages powered firing platform (302). Connector assembly (312) is configured to provide power to electronics and sensors positioned on or within linear surgical stapler (310). For example, connector assembly (312) may provide power from battery (254) positioned within powered firing platform (302) to a printed circuit board (314), a strain gauge (316), a plurality of sensors (322) and other electronics (not shown) on or within linear surgical stapler (310). Connector assembly (312) eliminates the need for an additional battery being placed within linear surgical stapler (310) to power sensors and electronics.

Powered firing platform (302) also differs from powered firing platform (202) in that powered firing platform (302) includes a platform processor (318). Platform processor (318) may include a memory (320) configured to store predetermined data or real time data relayed via connector assembly (312) from linear surgical stapler (310). Platform processor (318) is configured to apply a metered amount of voltage or current to actuator (230) when forward switch (248) is activated. Platform processor (318) may be in addition to or in place of forward relay (250). Platform processor (318) uses algorithms, predefined data parameters, and/or real time data to calculate the metered amount of voltage or current. Real time data is sent from sensors (322), which may include strain gages or photoelectric sensors for example, positioned on linear surgical stapler (310) via connector assembly (312) and/or printed circuit board (314). Powered surgical firing assembly (300) may additionally include a platform wireless device (324). Platform wireless device (324) includes a wireless transmitter and a wireless receiver configured to transmit and receive data from hub (304). Platform wireless device (324) may be Bluetooth® capable or include some other wireless compatibility known in the art to transmit and receive data without a wired connection. Hub (304) may include a hub wireless device (326) and a hub processor (328). Hub processor (328) may also include a hub memory (not shown) configured to store predefined data or real time data. Hub processor (328) may be configured to calculate firing data using algorithms, real time data, and predefined data. In some instances, data may be wirelessly sent back to platform processor (318) via hub wireless device (326) and platform wireless device (324).

In some instances, data received by platform processor (318) either directly from sensors (322) or from hub (304) may be used to enact "smart" firings in which the actuator (230) of powered firing platform (302) is controlled to thereby regular firing speed based on data signals provided by one or more sensors (322). For instance, in one example one or more of sensors (322) integrated into or on linear surgical stapler (310) may detect a specific color and therefore a specific type of a staple cartridge loaded into linear surgical stapler, and platform processor (318) may regulate the firing sequence (e.g., firing speed) accordingly. In the same or other examples, one or more of sensors (322) may detect a firing force applied to firing assembly (110) of linear surgical stapler (310), and platform processor (318) may regulate the firing sequence (e.g., firing speed) accordingly. Illustrative versions of such examples of "smart firing" are described in greater detail below.

In one example of a smart firing, a tissue thickness sensor (330) positioned within linear surgical stapler (310) transmits a tissue thickness data signal through connector assembly (312) to platform processor (318) and/or hub processor (328). Processor (318, 328) may then calculate suitable firing sequence data. Based upon the firing sequence data, platform processor (318) may regulate (e.g., increase or decrease) voltage supplied to motor (264), where an increased voltage increases the speed of motor (264) and thereby increases the firing speed, and where a reduced voltage reduces the speed of motor (264) and thereby decreases the firing speed.

In another example of a smart firing, a color sensor (332) positioned within linear surgical stapler (310) may be configured to detect a specific type of staple cartridge (340) loaded into linear surgical stapler (310) based on the color of the reload. Color sensor (332) may sense the color by printed circuit board (314) reading an RFID signature or another method known in art to determine a component electronically. Color data collected by color sensor (332) is transmitted to processor (318, 328) via connector assembly (312), which may then determine staple cartridge type based on detected color. Based on the determined cartridge type, platform processor (318) may regulate the speed of motor (264) and thus the firing speed accordingly, for example based on preferred firing speed data stored within memory (320). In that regard, color data may ultimately enable processor (318) to determine color-based firing data, which may include a preferred or expected firing speed based upon the color of staple cartridge (340).

Sensors (322) positioned in linear surgical stapler (310) may also transmit real time data to processor (318, 328). Real time data is transmitted to processor (318, 328) via connector assembly (312). Platform processor (318) may then change the firing speed of linear surgical stapler (310) based upon an algorithm that uses the color-based firing data, and/or real time data. Predetermined color-based firing data may be stored in memory (320). The color-based firing data and/or real time data may also be communicated to the user. Platform processor (318) may transmit color-based firing data and/or sensed firing data via wireless devices (324, 326) to hub processor (328). Hub processor (328) transmits the color firing data and/or sensed firing data to a hub user interface (334) such as a digital or LCD screen to be displayed. Platform processor (318) may also provide feedback to the user with a feedback device (336) positioned within housing (338). Feedback device may be in the form of a user interface (not shown), lights (not shown), or tactile feedback device (not shown).

FIG. 14A shows the linear surgical stapler (310) spaced apart from and aligned with powered firing platform (302). Powered firing platform (302) is provided in a retracted unfired position with pin (228) in a proximal position. First connector (306) is not engaging second connector (308) so that the stapler electronics (322, 330, 316, 314) is not in electrical communication with platform electronics (314, 318, 324, 336). Additionally, battery (254) does not power stapler electronics (322, 330, 316, 314).

FIG. 14B shows the linear surgical stapler (310) with linear surgical stapler installed within powered firing platform (302) in a retracted unfired position with pin (228) mated with pin aperture (17). First connector (306) is mated with second connector (308) forming connector assembly (312). Battery (254) provides power to the stapler electronics (314, 318, 324, 336). Connector assembly (312) provides electrical communication between stapler electronics (322, 330, 316, 314) and platform electronics (314, 318, 324, 336). Connector assembly (312) provides stapler electronics (322, 330, 316,314) electrical communication with hub (304) via the platform wireless device (324) and the hub wireless device (326).

III. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body having a cradle sized and configured to receive a linear surgical stapler operable to clamp and staple tissue with a plurality of staples; (b) an initiation device coupled with the body; (c) an actuator in communication with the initiation device; and (d) a driver operatively coupled with the actuator and configured to mechanically couple with a firing assembly of the linear surgical stapler, wherein the initiation device is configured to be manipulated by a user to activate the actuator so that the actuator actuates the driver relative to the body, thereby driving the firing assembly distally to fire the linear surgical stapler.

Example 2

The apparatus of Example 1, wherein the initiation device comprises an electrical switch.

Example 3

The apparatus of Example 2, wherein the actuator comprises a motor.

Example 4

The apparatus of Example 3, wherein the driver includes an engagement feature configured to mate with the firing assembly of the linear surgical stapler.

Example 5

The apparatus of Example 4, wherein the driver includes an elongate member extending distally along a longitudinal axis.

Example 6

The apparatus of Example 5, wherein the engagement feature includes a protrusion extending from a distal portion of the elongate member and is sized to be slidably received within an aperture of the linear surgical stapler.

Example 7

The apparatus of any of the previous Examples, wherein the body further comprises a handle configured to be gripped by a user.

Example 8

The apparatus of any of the previous Examples, further comprising a trigger movably coupled with the body and configured to be actuated by a user to activate the initiation device.

Example 9

The apparatus of any of the previous Examples, wherein the driver is actuatable by the actuator to drive the firing assembly of the linear surgical stapler distally relative to the body to fire the linear surgical stapler and subsequently retract the firing assembly proximally relative to the body to reset the linear surgical stapler.

Example 10

The apparatus of Example 9, wherein the driver is actuatable along a longitudinal axis of the body.

Example 11

The apparatus of Example 10, wherein the body includes a guide channel that extends along the longitudinal axis of the body, wherein the driver is slidably disposed within the guide channel.

Example 12

The apparatus of Example 9, wherein a distal end portion of the driver includes an elongate projection configured to extend at least partially through the linear surgical stapler and thereby engage the firing assembly of the linear surgical stapler.

Example 13

The apparatus of any of the previous examples, further comprising a processor in communication with the motor and the initiation device, wherein the processor is configured to communicate wirelessly with a remote processing unit.

Example 14

A powered surgical assembly comprising: (a) the apparatus of any of the previous examples, and (b) a linear surgical stapler.

Example 15

The powered surgical assembly of claim 14, wherein the apparatus includes a first electrical connector, and the linear surgical stapler includes a second electrical connector configured to electrically couple with the first electrical connector.

Example 16

An apparatus comprising: (a) a body having a cradle sized and configured to receive a linear surgical stapler operable to clamp and staple tissue with a plurality of staples; (b) a switch coupled with the body and configured to electrically communicate with a power supply; (c) a motor in electrical communication with the switch; and (d) a driver in mechanical communication with the motor and configured to couple with a firing assembly of the linear surgical stapler, wherein the switch is configured to be manipulated by a user to activate the motor so that the motor actuate the driver relative to the body, thereby driving the firing assembly distally to fire the linear surgical stapler.

Example 17

A powered surgical assembly comprising: (a) the apparatus of Example 16, wherein the cradle includes a first electrical connector; and (b) a linear surgical stapler, wherein the linear surgical stapler includes a second electrical connector configured to electrically couple with the first electrical connector.

Example 18

The powered surgical assembly of Example 17, wherein the linear surgical stapler includes a sensor, wherein the apparatus includes a processor configured to receive a sensor signal from the sensor via the first and second electrical connectors, wherein the processor is configured to wirelessly communicate data to a remote processing unit based on the received sensor signal.

Example 19

A powered surgical assembly, comprising: (a) a linear surgical stapler operable to clamp and staple tissue with a plurality of staples, wherein the linear surgical stapler includes a first electrical connector; and (b) a powered platform including: (i) a cradle configured to receive the linear surgical stapler, (ii) a second electrical connector configured to electrically couple with the first electrical connector, (iii) a switch configured to be in electrical communication with a power supply, (iv) a motor in electrical communication with the switch, (v) a driver operatively coupled with the motor, and (vi) a processor configured to electrically communicate with the linear surgical stapler via the first and second electrical connectors, wherein in response to actuation of the switch by a user, the motor is configured to actuate the driver to drive a firing assembly of the linear surgical stapler to thereby fire the linear surgical stapler, wherein the processor is operable to control the motor based on an electrical signal received from the linear surgical stapler via the first and second electrical connectors.

Example 20

The powered surgical assembly of Example 19, wherein the linear surgical stapler includes a sensor configured to transmit the electrical signal to the processor of the powered platform via the first and second electrical connectors.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Stapler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Surgical Stapler," issued Jun. 23, 2020; U.S. Pat. No. 10,898,187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgical Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022; U.S. Pat. No. 11,224,425, entitled "Surgical Linear Cutter Wishbone Separation Mechanism with Detent," issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021; U.S. patent application Ser. No. 17/489,879, entitled "Lockout Feature for Linear Surgical Stapler Cartridge," filed Sep. 30, 2021; U.S. patent application Ser. No. 29/842,580, entitled "Staple Cartridge for Linear Surgical Stapler," filed Jun. 16, 2022; and/or U.S. patent application Ser. No. 29/842,581, entitled "Linear Surgical Stapler," filed Jun. 16, 2022. The disclosure of each of these references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:

(a) a body having a cradle sized and configured to receive a linear surgical stapler operable to clamp and staple tissue with a plurality of staples;

(b) an initiation device coupled with the body;

(c) an actuator in communication with the initiation device; and (d) a driver operatively coupled with the actuator and configured to mechanically couple with a firing assembly of the linear surgical stapler, wherein a distal end of the driver includes a protrusion configured to be removably received within a through-hole of the firing assembly, wherein the initiation device is configured to be manipulated by a user to activate the actuator so that the actuator actuates the driver relative to the body, thereby driving the protrusion and the firing assembly distally relative to the body to fire the linear surgical stapler.

2. The apparatus of claim 1, wherein the initiation device comprises an electrical switch.

3. The apparatus of claim 2, wherein the actuator comprises a motor.

4. The apparatus of claim 1, wherein the body further comprises a handle configured to be gripped by a user.

5. The apparatus of claim 1, further comprising a trigger movably coupled with the body and configured to be actuated by a user to activate the initiation device.

6. The apparatus of claim 1, wherein the driver is actuatable by the actuator to drive the firing assembly of the linear surgical stapler distally relative to the body to fire the linear surgical stapler and subsequently retract the firing assembly proximally relative to the body to reset the linear surgical stapler.

7. The apparatus of claim 6, wherein the driver is actuatable along a longitudinal axis of the body.

8. The apparatus of claim 7, wherein the body includes a guide channel that extends along the longitudinal axis of the body, wherein the driver is slidably disposed within the guide channel.

9. The apparatus of claim 1, further comprising a processor in communication with the motor and the initiation device, wherein the processor is configured to communicate wirelessly with a remote processing unit.

10. A powered surgical assembly comprising:

(a) the apparatus of claim 1, and (b) a linear surgical stapler.

11. The powered surgical assembly of claim 10, wherein the apparatus includes a first electrical connector, and the linear surgical stapler includes a second electrical connector configured to electrically couple with the first electrical connector.

12. The powered surgical assembly of claim 10, wherein the linear surgical stapler comprises a first stapler half, a second stapler half configured to removably couple with the first stapler half, and a firing assembly having an opening configured to slidably receive the protrusion of the driver.

13. The apparatus of claim 1, wherein the actuator comprises an air solenoid.

14. The apparatus of claim 1, further comprising a power supply including a compressed gas.

15. An apparatus comprising:

(a) a body having a cradle sized and configured to receive a linear surgical stapler operable to clamp and staple tissue with a plurality of staples;

(b) a switch coupled with the body and configured to electrically communicate with a power supply;

(c) a motor in electrical communication with the switch; and (d) a driver in mechanical communication with the motor and configured to couple with a firing assembly of the linear surgical stapler, wherein a distal end of the driver includes a protrusion configured to be removably received within an opening of the firing assembly, wherein the switch is configured to be manipulated by a user to activate the motor so that the motor actuates the driver relative to the body, thereby driving the protrusion and the firing assembly distally relative to the body to fire the linear surgical stapler.

16. A powered surgical assembly comprising:

(a) the apparatus of claim 15, wherein the cradle includes a first electrical connector; and (b) a linear surgical stapler, wherein the linear surgical stapler includes a second electrical connector configured to electrically couple with the first electrical connector.

17. The powered surgical assembly of claim 16, wherein the linear surgical stapler includes a sensor, wherein the apparatus includes a processor configured to receive a sensor signal from the sensor via the first and second electrical connectors, wherein the processor is configured to wirelessly communicate data to a remote processing unit based on the received sensor signal.

18. The apparatus of claim 15, wherein the opening of the firing assembly comprises a through-hole.

19. A powered surgical assembly, comprising:

(a) a linear surgical stapler operable to clamp and staple tissue with a plurality of staples, wherein the linear surgical stapler includes a first electrical connector and a firing assembly; and (b) a powered platform including:

(i) a cradle configured to receive the linear surgical stapler, (ii) a second electrical connector configured to electrically couple with the first electrical connector, (iii) a switch configured to be in electrical communication with a power supply, (iv) a motor in electrical communication with the switch, (v) a driver operatively coupled with the motor, wherein a distal end of the driver includes a protrusion configured to be removably received within an opening of the firing assembly, and (vi) a processor configured to electrically communicate with the linear surgical stapler via the first and second electrical connectors, wherein in response to actuation of the switch by a user, the motor is configured to actuate the driver to drive the protrusion and the firing assembly of the linear surgical stapler distally relative to the cradle to thereby fire the linear surgical stapler, wherein the processor is operable to control the motor based on an electrical signal received from the linear surgical stapler via the first and second electrical connectors.

20. The powered surgical assembly of claim 19, wherein the linear surgical stapler includes a sensor configured to transmit the electrical signal to the processor of the powered platform via the first and second electrical connectors.

* * * * *